US011009498B2

(12) United States Patent
Alden et al.

(10) Patent No.: US 11,009,498 B2
(45) Date of Patent: May 18, 2021

(54) NANOPORE-CONTAINING SUBSTRATES WITH ALIGNED NANOSCALE ELECTRONIC ELEMENTS AND METHODS OF MAKING AND USING SAME

(71) Applicant: Cornell University, Ithaca, NY (US)

(72) Inventors: Jonathan Alden, Ithaca, NY (US); Alejandro Cortese, Ithaca, NY (US); Arthur Barnard, Hayward, CA (US); Paul McEuen, Newfield, NY (US)

(73) Assignee: Cornell University, Ithaca, NY (US)

( * ) Notice: Subject to any disclaimer, the term of this patent is extended or adjusted under 35 U.S.C. 154(b) by 798 days.

(21) Appl. No.: 15/531,956

(22) PCT Filed: Dec. 1, 2015

(86) PCT No.: PCT/US2015/063224
§ 371 (c)(1),
(2) Date: May 31, 2017

(87) PCT Pub. No.: WO2016/094131
PCT Pub. Date: Jun. 16, 2016

(65) Prior Publication Data
US 2017/0315109 A1 Nov. 2, 2017

Related U.S. Application Data

(60) Provisional application No. 62/085,795, filed on Dec. 1, 2014.

(51) Int. Cl.
*G01N 33/487* (2006.01)
*G01N 33/543* (2006.01)
(Continued)

(52) U.S. Cl.
CPC ..... *G01N 33/48721* (2013.01); *C12Q 1/6869* (2013.01); *G01N 27/4145* (2013.01);
(Continued)

(58) Field of Classification Search
CPC ........ G01N 33/48721; G01N 27/4145; G01N 27/4146; G01N 27/44791; G01N 33/54366; C12Q 1/6869
See application file for complete search history.

(56) References Cited

U.S. PATENT DOCUMENTS 5,795,782 A    8/1998    Church et al.
6,905,586 B2    6/2005    Lee et al.
(Continued)

FOREIGN PATENT DOCUMENTS

CN        101225436 A    7/2008
CN        102183630 A    9/2011
(Continued)

OTHER PUBLICATIONS

J. Ma, et al. "Diameters of single-walled carbon nanotubes (SWCNTs) and related nanochemistry and nanobiology", Frontiers of Materials Science in China, 4(1): p. 17-28, Mar. 2010.*
(Continued)

*Primary Examiner* — J. Christopher Ball
(74) *Attorney, Agent, or Firm* — Hodgson Russ LLP

(57) ABSTRACT

A nanopore-containing substrate includes a substrate, a membrane on the substrate, and at least one nanoscale electronic element disposed on or embedded in the membrane. The membrane defines at least one nanopore. The nanoscale electronic element is aligned with one of the nanopores such that a shortest distance between an edge of the nanoscale electronic element and the edge of the nanopore is less than 50 nm. The nanopores may be formed by etching through a dielectric layer using a solution while applying a voltage to the nanoscale electronic element relative to the solution. The nanopore-containing substrate can be used to detect or sequence a biopolymer, such as a
(Continued)

nucleic acid. The nanopore-containing substrate may be used with a biopolymer detection and/or sequencing system.

16 Claims, 30 Drawing Sheets

(51) Int. Cl.
  *C12Q 1/6869* (2018.01)
  *G01N 27/414* (2006.01)
  *G01N 27/447* (2006.01)

(52) U.S. Cl.
  CPC ... *G01N 27/4146* (2013.01); *G01N 27/44791* (2013.01); *G01N 33/54366* (2013.01)

(56) References Cited

U.S. PATENT DOCUMENTS

| | | | |
|---|---|---|---|
| 8,470,408 | B2 | 6/2013 | Branton et al. |
| 8,628,649 | B2 | 1/2014 | Lindsay et al. |
| 2003/0207326 | A1* | 11/2003 | Su .............. G01N 33/6803 435/7.1 |
| 2006/0019259 | A1 | 1/2006 | Joyce |
| 2007/0190542 | A1 | 8/2007 | Ling et al. |
| 2009/0136682 | A1 | 5/2009 | Branton et al. |
| 2011/0227558 | A1 | 9/2011 | Mannion et al. |
| 2013/0062206 | A1 | 3/2013 | Afzali-Ardakani et al. |
| 2013/0299448 | A1 | 11/2013 | Stolovitzky et al. |
| 2014/0152330 | A1 | 6/2014 | Afzali-Ardakani et al. |
| 2015/0108008 | A1 | 4/2015 | Kwok et al. |

FOREIGN PATENT DOCUMENTS

| | | |
|---|---|---|
| CN | 102384934 A | 3/2012 |
| WO | WO-2013167955 A1 * | 11/2013 |

OTHER PUBLICATIONS

Branton, D., et al., the Potential and Challenges of Nanopore Sequencing, Nature Biotechnology, 2008, vol. 26, No. 10, pp. 1146-1153. https://dash.harvard.edu/bitstream/handle/1/2664284/22ManuscriptSynthesisWithFigures.pdf?sequence=4.

Miles, et al., Single molecule sensing with solid-state nanopores: novel materials, methods, and applications, Chem. Soc. Rev., Jan. 2013, vol. 42, No. 1, pp. 15-28.

Venta, et al., Differentiation of Short, Single-Stranded DNA Homopolymers in Solid-State Nanopores, ACS Nano, vol. 7, No. 5, pp. 4629-4636 Apr. 26, 2013.

Larkin, et al., Slow DNA Transport through Nanopores in Hafnium Oxide Membranes, ACS Nano, vol. 7, No. 11, pp. 10121-10128 Oct. 1, 2013.

Xie, et al., Local electrical potential detection of DNA by nanowire-nanopore sensors, Nature Nanotechnology, vol. 7, pp. 119-125 Dec. 11, 2011.

Traversi, et al., Detecting the translocation of DNA through a nanopore using graphene nanoribbons, Nature Nanotechnology, vol. 8, pp. 939-945 Nov. 17, 2013.

Sadki, et al., Embedding a carbon nanotube across the diameter of a solid state nanopore, J. Vac. Sci. Technol. B, vol. 29, No. 5, pp. 053011, 4 pages Sep. 1, 2011.

Vlassarev, DNA Characterization with Solid-State Nanopores and Combined Carbon Nanotube across Solid-State Nanopore Sensors, Harvard Physics PhD Thesis, 135 pages May 1, 2012.

Kumar et al., Noise and its reduction in graphene based nanopore devices, Nanotechnology, vol. 24, No. 49, pp. 1-7. Nov. 15, 2013.

Taniguchi et al., Fabrication of the gating nanopore device, Applied Physics Letters, vol. 95, No. 12 pp. 1-3. Sep. 22, 2009.

Fanget et al., Nanopore Integrated Nanogaps for DNA Detection, Nano Letters, vol. 14, pp. 244-249 Dec. 9, 2013.

* cited by examiner

A B

NANOPORE-CONTAINING SUBSTRATES WITH ALIGNED NANOSCALE ELECTRONIC ELEMENTS AND METHODS OF MAKING AND USING SAME

CROSS-REFERENCE TO RELATED APPLICATIONS

This application claims priority to the provisional patent application filed Dec. 1, 2014 and assigned U.S. App. No. 62/085,795, the disclosure of which is hereby incorporated by reference.

STATEMENT REGARDING FEDERALLY-SPONSORED RESEARCH OR DEVELOPMENT

This invention was made with government support under contract no. FA9950-10-1-0410 awarded by the Air Force Office of Scientific Research and contract no. FA9550-09-1-0705 awarded by the Office of Naval Research. The government has certain rights in the invention.

FIELD OF THE DISCLOSURE

This disclosure relates to nanopore-containing substrates.

BACKGROUND OF THE DISCLOSURE

In the nanopore-based sequencing space, one demonstration of sequencing involved measuring ionic current flowing through a channel protein embedded in a membrane as DNA passed through. This method is limited in that it requires biological materials to be part of the device, which tend to be less durable than non-organic materials. It also involves slowing the DNA down to approximately 1 ms per nucleotide in order to obtain sufficient signal-to-noise. Another limitation is that it is not easily parallelizable, since only one pore per microfluidic channel can be used.

In the solid-state nanopore-based sequencing space, current methods have relied primarily on measuring ionic current through solid-state nanopores (e.g., silicon nitride, graphene, hafnia) that have been formed by etching with ion beam or electron beam, which involves a high-vacuum system that tends not to scale well to an industrial process. Furthermore, there have been no demonstrations of sequencing. To date, the best demonstrations with solid-state pores have distinguished between different 30-nucleotide long single-stranded DNA molecules (e.g., 30 adenines, 30 cytosines, etc.).

In the area of solid-state nanopore-based sequencing with field-effect readout, one demonstration involved using a 50 nm-wide silicon nanowire with a nearby pore. Approximately 3000 nucleotide double-stranded DNA was detected, but no sequence information was obtained. Another demonstration involved using a graphene nanoribbon to detect approximately 3000 nucleotide double-stranded DNA plasmids, but no sequence information was obtained. Both of these methods have the same limitations associated with producing nanopores using an electron beam. Additionally, the electron beam may damage the field-effect nanoscale device (nanowire or nanoribbon). The nanowire method also has the limitation that the 50 nm width of the wire is approximately 150 times the separation between nucleotides in DNA. One limitation of the graphene nanopore is that graphene nanoribbons have dangling bonds at their edges, making them both more reactive than nanotubes, and making their electrical properties highly variable.

BRIEF SUMMARY OF THE DISCLOSURE

In a first embodiment, a nanopore-containing substrate is provided. The nanopore-containing substrate includes a substrate, a membrane disposed on the substrate, and at least one nanoscale electronic element that is disposed on or in the membrane. The membrane defines at least one nanopore through the membrane. The nanopore is configured to provide fluidic communication between opposite sides of the membrane. The nanoscale electronic element is capable of conducting electricity and is different from the membrane with respect to at least one of shape, material composition, electrical conductivity, or chemical bonding. The nanoscale electronic element is aligned with the nanopore such that a shortest distance between an edge of the nanoscale electronic element and an edge of the nanopore is less than 50 nm.

The substrate may be fabricated of silicon, quartz, fused silica, sapphire, gallium arsenide, and/or silicon carbide. The membrane may be fabricated of a dielectric material such as silicon nitride, alumina, hafnium oxide, tantalum oxide, silicon dioxide, and/or boron nitride. The membrane also may be fabricated of a semiconductor or a semimetal such as a metal dichalcogenide, graphene, silicon, germanium, and/or gallium arsenide. The membrane can have a thickness from 0.3 nm to 1,000 nm.

The nanoscale electronic element can include a carbon nanotube, graphene, a metal, a metallic or semiconducting nanowire, a metal or semiconducting electrode with a thickness less than 20 nm, or a gap between two electrodes. The shortest distance between the edge of the nanoscale electronic element and the edge of the nanopore may be less than 10 nm or less than 1 nm. The edge of the nanoscale electronic element may intersect the edge of the nanopore. The nanoscale electronic element can be positioned parallel to a normal vector defining a plane of a surface of the membrane surrounding the nanopore. The nanoscale electronic element may be in electrical contact with an electrical circuit.

The nanopore can have a depth through the membrane from 0.3 nm to 1,000 nm. The nanopore can have a width dimension from 1 nm to 50 nm or from 1 nm to 20 nm.

The nanoscale electronic element can be functionalized with a functional group. The functional group can be a carboxyl group, a hydroxyl group, an amine group, a thiol group, a single nucleotide, a sequence of nucleotides, an amino acid, a polypeptide, and/or a protein. The nanoscale electronic element also can be coated with a dielectric.

In an instance, there may be a plurality of the nanoscale electronic elements. The plurality of the nanoscale electronic elements forms an array disposed on or in the membrane. Two of the nanoscale electronic elements may be in contact with one another.

In another instance, there may be a plurality of the nanoscale electronic elements and a plurality of the nanopores. The plurality of the nanoscale electronic elements forms an array disposed on or in the membrane. Each of the nanopores has one of the nanoscale electronic elements aligned to the nanopore such that a shortest distance between an edge of the nanoscale electronic element and an edge of the nanopore is less than 50 nm.

The nanoscale electronic element may not have been exposed to an electron beam or ion beam having an average accelerating voltage greater than 1 kV. The nanoscale electronic element also may not have been exposed to an electron beam or an ion beam.

A dimension of the nanoscale electronic element perpendicular to a direction of current flow through the nanoscale electronic element may not exceed 20 nm or may not exceed 10 nm.

In a second embodiment, a method is provided. In the method, at least one nanoscale electronic element capable of conducting electricity is disposed on or in a membrane disposed on a substrate. The membrane is fabricated of a dielectric, semiconductor, or semimetal. The membrane is contacted with an etchant. A voltage is applied to the nanoscale electronic element relative to another electrode in contact with the etchant such that at least one nanopore is etched through the membrane. A nanopore-containing substrate may be formed.

Space between the nanoscale electronic element and the etchant may be occupied by a portion of the membrane prior to applying the voltage. The etchant also may contact the nanoscale electronic element while applying the voltage.

The etchant can include hydrofluoric acid, phosphoric acid, potassium hydroxide, and/or tetramethylammonium hydroxide.

The voltage may be pulsed, ramped, constant, or a combination thereof. A sign and/or a magnitude of the voltage can be selected to locally affect etch rate of the etchant proximate the nanoscale electronic element.

In an instance, a pressure is applied to fluid on one side of the membrane relative to an opposite side of the membrane. The fluid flows through the nanopore after the nanopore is etched through the membrane. The fluid does not substantially etch the membrane and decreases or halts etching of the membrane.

In an instance, formation of the nanopore is detected by applying a second voltage to a detection electrode and monitoring current flowing to or from the detection electrode. The detection electrode is separate from the nanoscale electronic element and is positioned outside the etchant. A voltage may be applied to a solution on a side of the membrane opposite the etchant using the detection electrode. The detection electrode may be fabricated of a metal and is positioned on a side of the membrane opposite the etchant. The detection electrode may be electrically insulated from the nanoscale electronic element by a dielectric or a semiconductor.

Etching of the nanopore may be stopped using feedback. The feedback can be optical and based on at least one of: visible etching of a side of the membrane opposite the etchant; visible accumulation of fluid or formation of crystals at a location of the nanopore; and/or fluorescence activated by formation of the nanopore or interaction of fluorescent dyes with the nanoscale electronic element, the etchant, and/or material that comes into contact with the fluorescent dye due to etching of the nanopore. The feedback also can be electrical and based on at least one of: changes in current from one side of the membrane to an opposite side of the membrane; changes in current and/or conductance through the nanoscale electronic element; and/or changes in current flowing between the nanoscale electronic element and the electrode in contact with the etchant. Stopping may occur when a magnitude of a current exceeds a threshold. Stopping may occur when a rate of change of a current or derivative of current with respect to time exceeds a threshold. Stopping may occur when a shape of a plot of current through the nanoscale electronic element as a function of voltage of a detection electrode and/or the electrode in contact with the etchant changes. For example, gating characteristics and/or capacitance of the nanoscale electronic element changes.

Etching of the nanopore also may be stopped after a designated time.

Etching of the nanopore may be stopped by replacing the etchant with a fluid that is less chemically-reactive than the etchant. Etching of the nanopore also may be stopped by changing the voltage to the nanoscale electronic element.

A size of the nanopore may be determined based on current.

A plurality of the nanopores may be formed. Each of the plurality of the nanopores can be aligned to a different nanoscale electronic element. Electrical feedback can be monitored for each of the nanoscale electronic elements. Etching of the nanopore can be stopped at one of the plurality of nanoscale electronic elements by changing the voltage to the one of the plurality of nanoscale electronic elements that has a shortest distance between an edge of the nanoscale electronic element and an edge of the nanopore of less than 50 nm.

During etching of the nanopore, an average electric field along a shortest distance between any region of the nanoscale electronic element disposed on or in the membrane and the etchant may be less than 0.1 V/nm. Etching the nanopore may be non-monotonic with the voltage.

Applying the voltage may include applying a first voltage whereby the membrane is thinned and applying a second voltage smaller than the first voltage to form the nanopore.

Applying the voltage also may include applying a first voltage to the nanoscale electronic element relative to the electrode in contact with the etchant whereby etching of the membrane is induced; applying a second voltage to the nanoscale electronic element relative to the electrode in contact with the etchant; monitoring current from the etchant to the nanoscale electronic element while the second voltage is applied; detecting an increase in the current from the etchant to the nanoscale electronic element; and removing the first voltage and the second voltage when the nanopore is formed. The second voltage induces an electric field of less than 0.1 V/nm across the membrane.

In a third embodiment, a method is provided. In the method, a solution containing a biopolymer flows through the nanopore of the membrane of a nanopore-containing substrate. The biopolymer in the solution is detected and/or sequenced using the nanoscale electronic element. The biopolymer may be a nucleic acid. Distinguishing between a single-stranded nucleic acid and double-stranded nucleic acid can be performed using the nanoscale electronic element. The biopolymer may be constrained in the nanopore and move linearly past the nanoscale electronic element. The solution may be electrophoretically driven through the nanopore. Ionic current through the nanopore and current through the nanoscale electronic element can be monitored simultaneously. The nanoscale electronic element may be a transistor detecting the biopolymer by means of the field-effect.

In a fourth embodiment, a device is provided. The device includes a nanopore-containing substrate and a biopolymer detection and/or sequencing system connected with the nanopore-containing substrate. A data recording system may be connected with the biopolymer detection and/or sequencing system.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Figure 1:
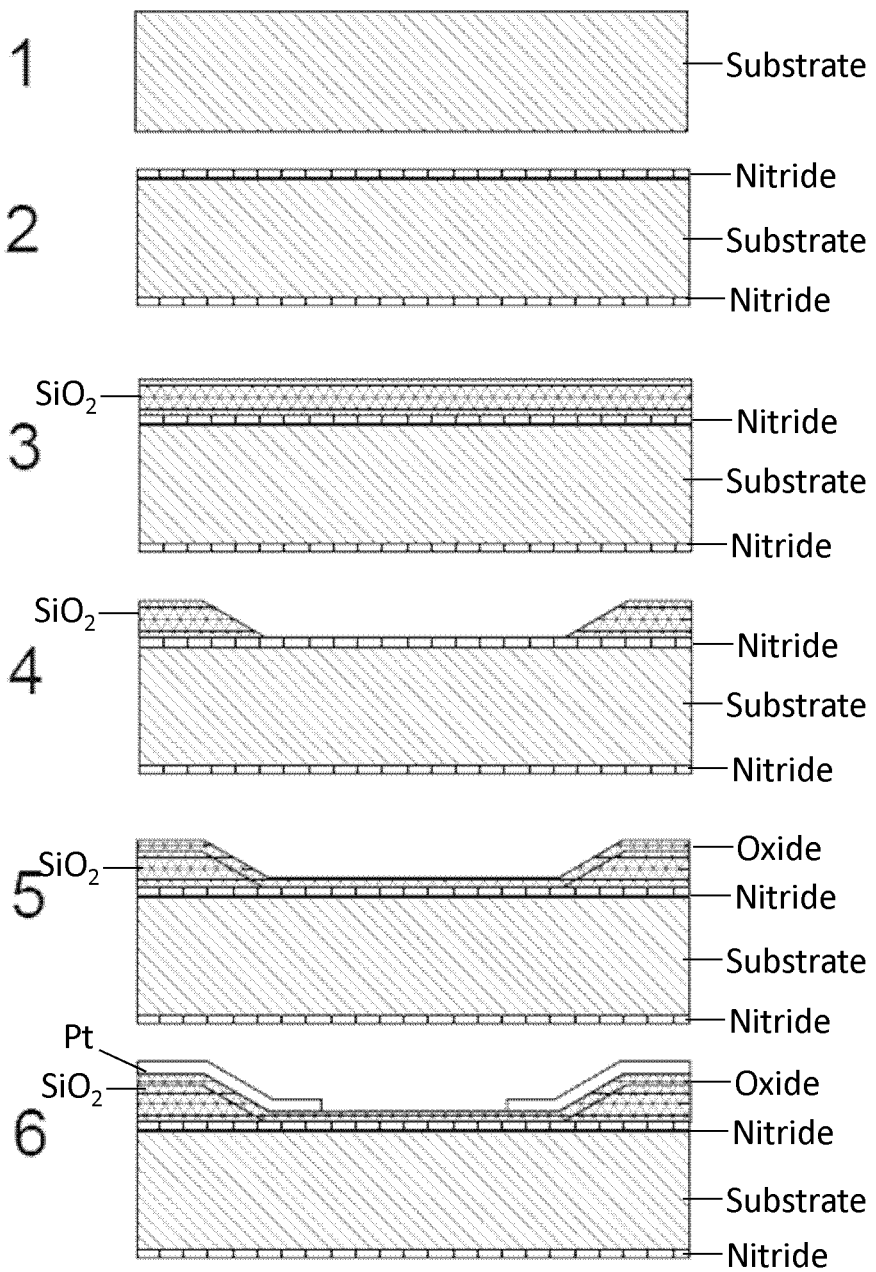
FIG. 1. Example of nanotube-aligned nanopore device fabrication. (1) The devices are made on a double-side-polished high resistance silicon (>10 kΩ-cm) substrate to minimize capacitive coupling between substrate and device. (2) 16 nm of high-quality thermal nitride is grown on both sides of the substrate. (3) 1.4 μm of silicon dioxide is grown on top of the wafer using plasma-enhanced chemical vapor deposition (PECVD). (4) The wafer is patterned with photoresist and the silicon dioxide is removed using 30:1 buffered oxide etch (BOE), which undercuts the resist to leave a gradually-sloping oxide layer (over which electrodes are evaporated). (5) 70 nm of oxide is grown using PECVD. The oxide was removed and regrown to ensure a smooth surface, since the BOE-etched surface tends to be rough. (6) 25 nm-thick platinum electrode pairs, separated by 20 μm are deposited following the deposition of a 5 nm chrome adhesion layer. This layer also contains the alignment marks for all remaining layers. (7) 30:1 BOE is used to etch a 4 μm windows between electrode pairs. This difference in dielectric thickness will later ensure that the nanopore formation occurs within this window, and not elsewhere under the nanotube or electrode. (8) Using backside alignment, a window is patterned on the back of the wafer in the device region, and the nitride there is removed by reactive ion etching (RIE) ($CHF_3/O_2$). A larger region surrounding the device is also etched to define the edges of what will later become the TEM grid. (9) Using 30:1 BOE, a window outside of the TEM grid area (far left) is opened in the silicon dioxide. (10) Using RIE ($CHF_3/O_2$), the nitride is removed from this window. (11) Copper wires are evaporated to connect the platinum electrodes to the silicon substrate. This will later be used to ensure that charge build-up on the electrodes does not destroy the carbon nanotube device, particularly during imaging with scanning electron microscope (SEM). (12) Iron catalyst particles are evaporated onto a Y-cut quartz substrate in 5 μm lines, separated by 100 μm. Arrays of parallel nanotubes are then grown from methane using chemical vapor deposition (CVD). (13) 50 nm of polymethylmethacrylate (PMMA) is spun over the nanotubes. (14) The PMMA and nanotubes are separated from the quartz by placing in 1M KOH for an hour, then removed and dipped into water. When lowering into the water, the PMMA/nanotubes lift off the quartz and float on the surface. (15) The PMMA/nanotubes are scooped out of the water using the original patterned substrate. The device is dried with a nitrogen gun, then baked at 90° C. for a minute. (16) The PMMA is removed by dissolving in acetone, then rinsing with isopropyl alcohol (IPA). (17) The nanotubes are patterned and etched away everywhere except in the device area, using oxygen plasma. The resist is removed with acetone and IPA. The device is baked at 225° C. for 30 minutes to reduce remaining polymer residue. At this point, the device is imaged using SEM, to determine which pairs of electrodes have single nanotubes between them. (18) 10 nm of aluminum oxide, followed by 15 nm of silicon dioxide are deposited using atomic layer deposition (ALD). A 2-3 nm layer of hafnia or tantalum oxide may be deposited prior to this layer to potentially reduce the size of nanopores that are later formed. (19) A gold top gate is evaporated over the device area with minimal overlap with the platinum electrodes. (20) The device of (19) showing edge of TEM grid. (21) The ALD silicon dioxide and aluminum oxide are removed using 30:1 BOE followed by MIF 726 developer (dilute TMAH). (22) The copper is them removed using ferric chloride (Transene CE 200). (23) A 5 μm thick polymer base-protection (Protek B3) layer is spun onto the surface. (24) 80 nm of gold is evaporated over this. 5 μm of gold is then electroplated over this seed layer. This gold layer may be added because the polymer protection layer can have pinholes in it, and a single pinhole will allow KOH to undercut the entire aluminum oxide layer in a matter of minutes. (25) The device is placed in 20% potassium hydroxide (KOH) to etch open a window from the bottom of the device by etching the silicon substrate. This also separates the wafer into hundreds of TEM grids. (26) The polymer layer is removed using 1165 remover (N-methyl pyrrolidone), lifting off the gold layer. The surface is cleaned using oxygen plasma. (27) A nanopore is then etched by flowing 100:1 (49%) HF below the device, while applying a positive voltage to the nanotube, relative to the HF solution, and periodically sweeping the voltage on the gold top gate to determine whether a nanopore has formed. When a current is detected, the voltage on the nanotube is turned off, and the HF is flushed out with water. (28) Gold etchant (potassium iodide) is used to remove the gold top gate. The device is then rinsed in water. The water is gradually exchanged with methanol and the device is dried. (29) Microfluidic channels are placed on top and bottom. The channels are made from polydimethylsiloxane (PDMS) clamped between acrylic holders with larger fluidic channels that were formed using a $CO_2$ laser and hotpress bonding. This apparatus can then attach to standard microfluidic tubing.
Figure 1:
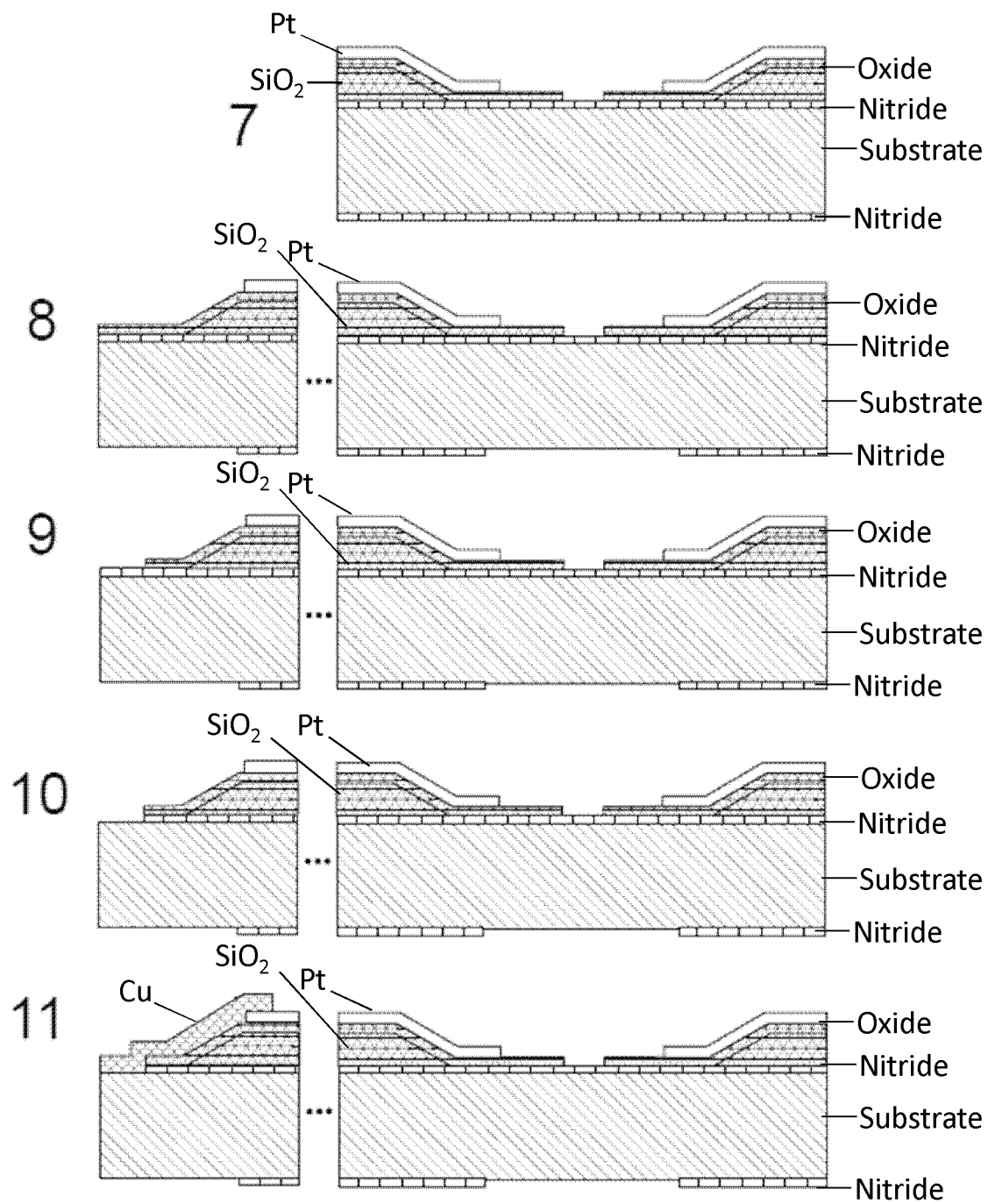
Figure 1:
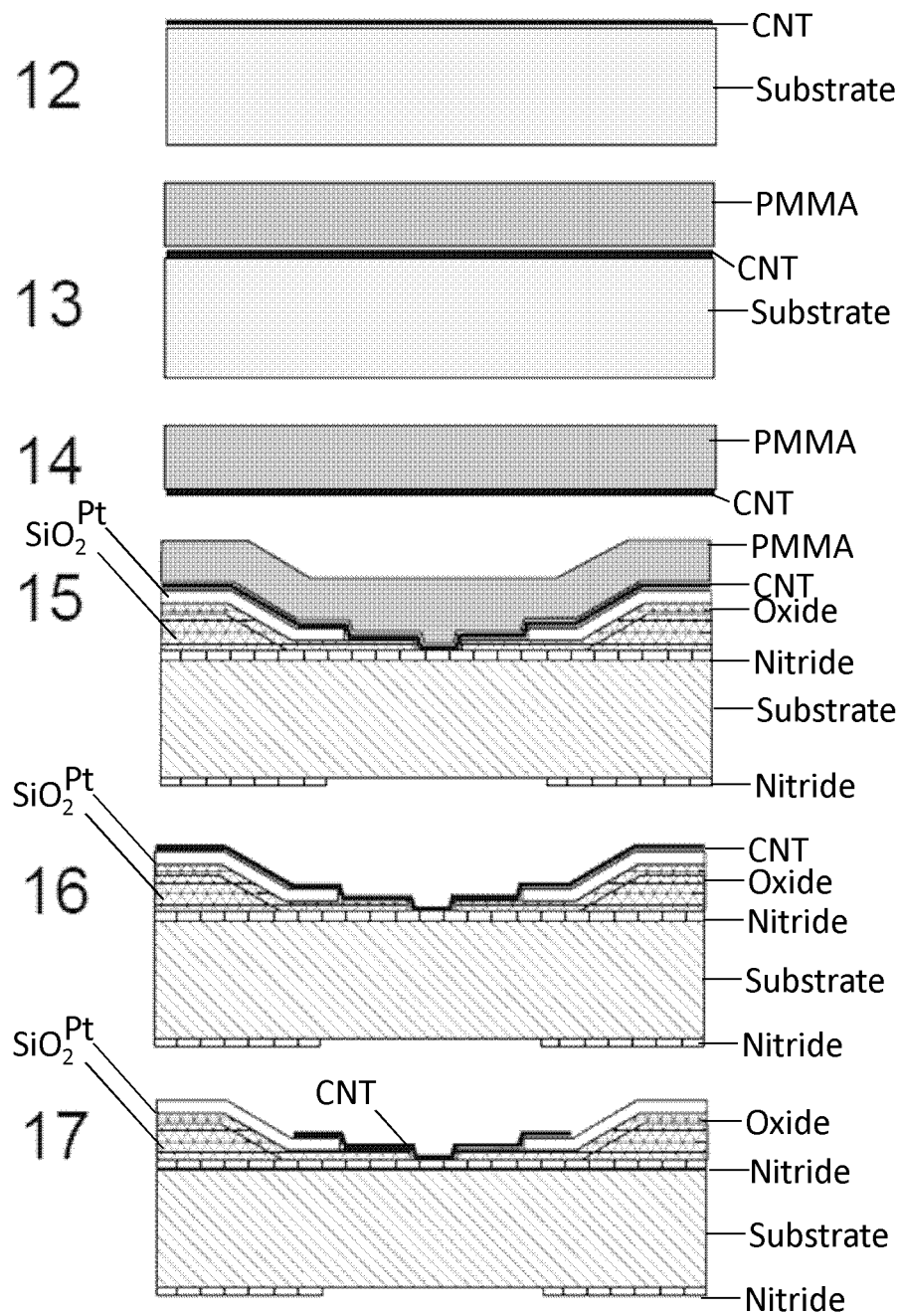
Figure 1:
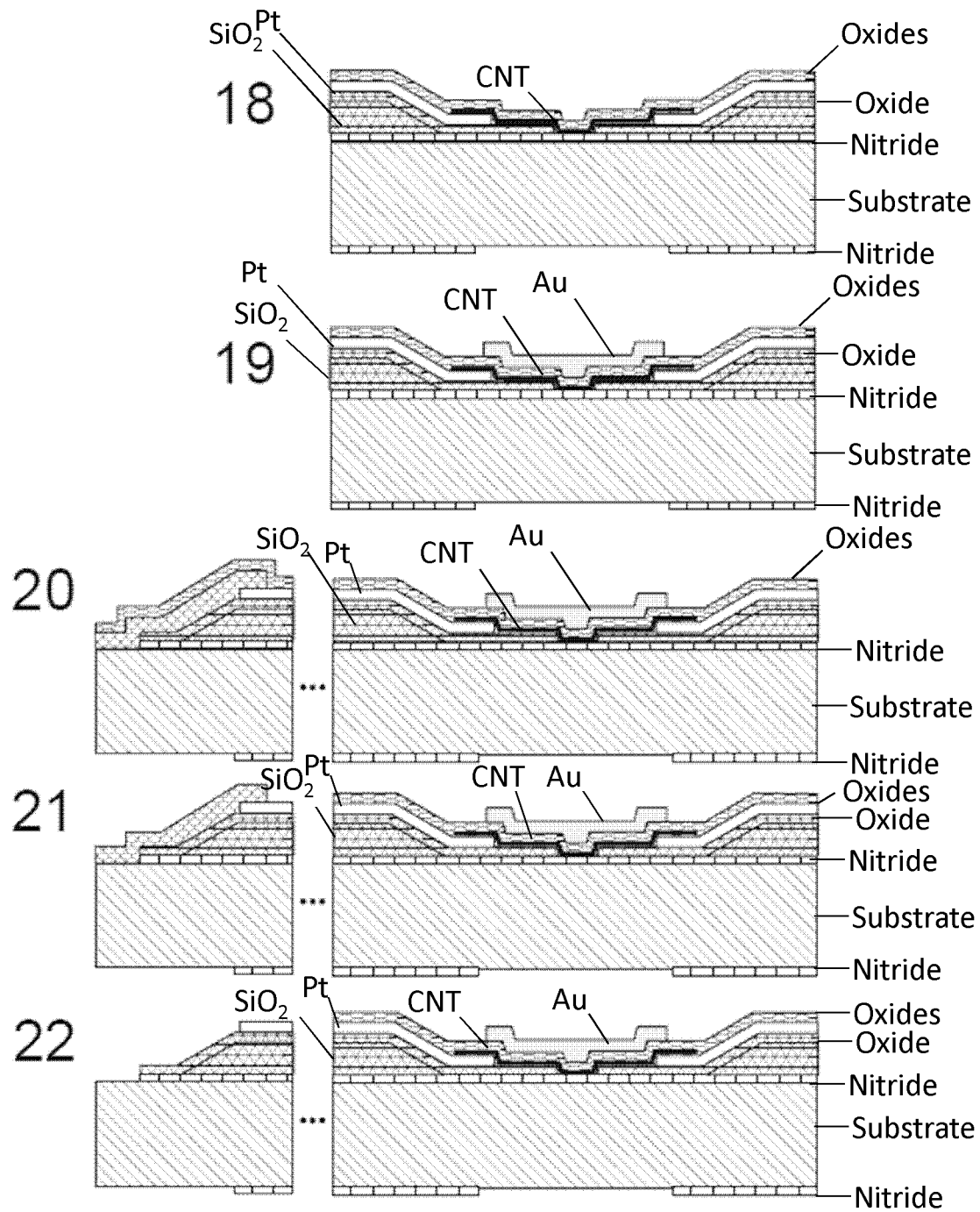
Figure 1:
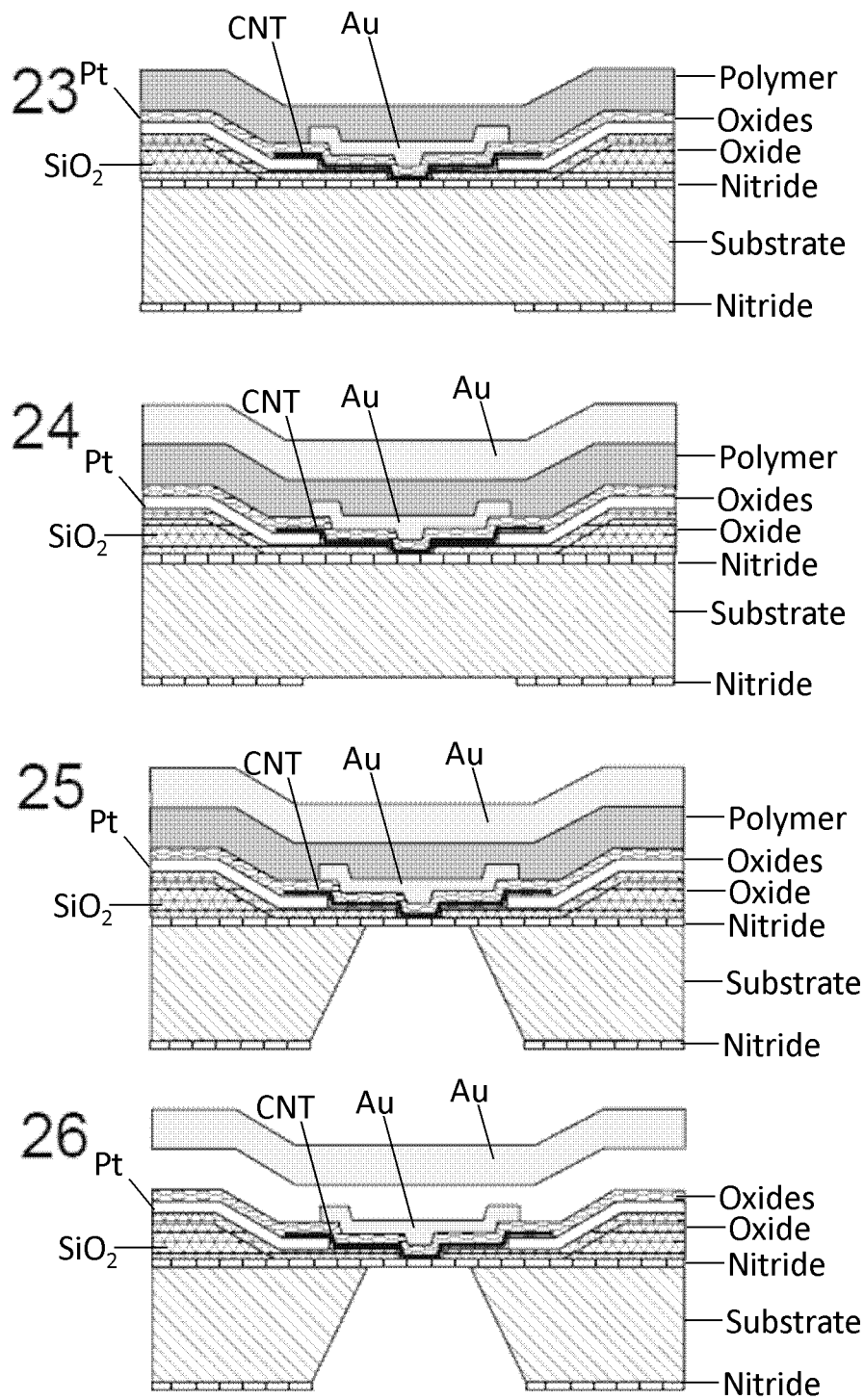
Figure 1:
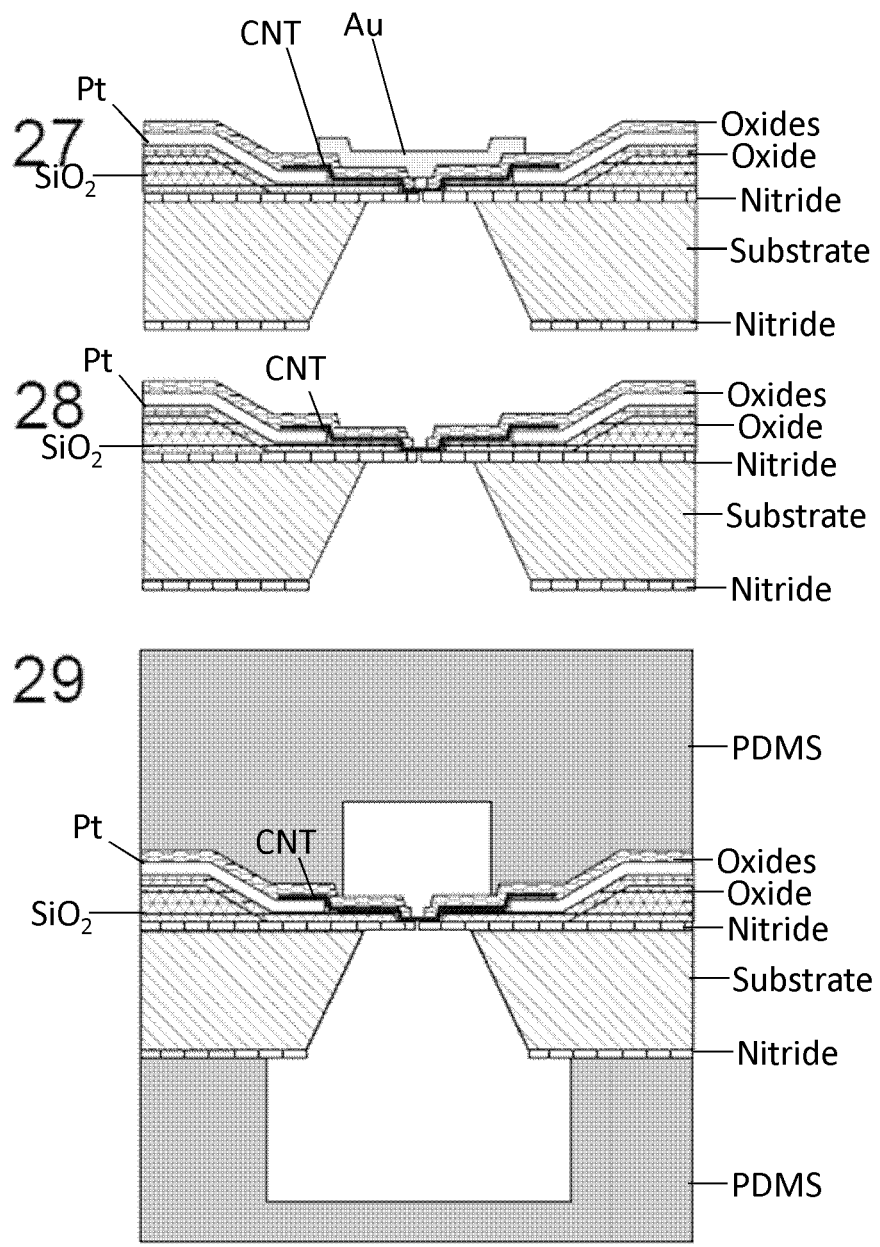

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

The present disclosure provides nanopore-containing substrates with nanoscale electronic elements aligned to the nanopores of the substrate. Also provided are methods of making and using such substrates and a device using such substrates with a biopolymer detection and/or sequencing system.

The present disclosure provides many unique features. Nanopores are fabricated using chemical methods, making them more industrially-scalable than electron-beam or ion-beam based methods, and avoiding the damage to nearby nanostructures that is common with these latter methods. Nanopores are fabricated in a way that they are self-aligned to electrically-conducting nanoscale electronic elements, which, in this case, may be carbon nanotubes. Nanopores are fabricated that are substantially perpendicular (e.g., perpendicular) to electrically conducting nanoscale electronic elements. Nanopores can be reliably aligned to a nanoscale electronic element by using an applied voltage to locally enhance a chemical etch. Electric fields below that required for dielectric breakdown may be used, thus avoiding the damage to the sensitive nanoscale electronic elements that is otherwise common.

Etching of a dielectric is locally enhanced by applying a voltage to a nearby electrically-conducting material relative to a solution potential. Electrical feedback may be used during the process of etching the nanopores, stopping the nanopore formation when the nanopore has a diameter of, for example, 1-15 nm. The size of the nanopores may be self-limited. For example, it is expected that a back-pressure of gas or liquid may be used to self-limit the size of the nanopore, by forcing the etchant solution away from the nanopore once it forms.

Etching can refer to a subtractive process using etching chemicals to remove material. In an instance, the etchant, in the absence of any applied voltage(s), etches the membrane at a rate of at least 2 nm/hour under the conditions used for the nanopore etching.

A secondary electrode (the top gate) separated from the nanotube by a dielectric (e.g., aluminum oxide) is used for the etch detection, reducing the possibility that the etchant etches the nanoscale electronic element (e.g., carbon nanotube). The nanoscale electronic element can also be used for this purpose, but may be susceptible to attack from the etchant, and may have less desirable detection characteristics (e.g., lower signal-to-noise, lower electrochemical activity, etc.).

The dielectric separating the "detection electrode" from the nanoscale electronic element and nanopore is etchable by the etchant (at a high rate) allowing for isolation from the nanoscale electronic element during the nanopore etch, but rapid removal once the nanopore is etched through, allowing for rapid detection of the nanopore formation. An ionic solution (and electrochemically active electrode) may also be used in place of the detection electrode.

This nanopore-fabrication method, with feedback, may also be applied to other systems such as localizing a single nanopore under a 2d electrode such as graphene, which could then be etched to form a one-atom-thick conducting element, with a nanopore through which a biopolymer could be translocated. This is expected to provide significantly reduced capacitance relative to existing methods, and involves nanopore formation without an electron beam or ion beam.

A nanopore-aligned nanotube may be etched from the back-side, through the nanopore, to create a tunnel junction which is expected to provide increased sensitivity to individual nucleotides.

A nanopore-aligned nanotube may be functionalized by chemicals flowing through the nanopore to add chemical groups with enhanced sensitivity and/or selectivity in order to, for example, distinguish between nucleotides.

After nanopore formation, the nanotube may be selectively coated where it rests on the substrate (e.g., by atomic layer deposition), leaving the nanotube exposed to solution only at the nanopore. Alternatively the entire nanotube and nanopore may be coated, then the nanopore re-opened from the bottom leaving the nanotube exposed to solution only at the nanopore (e.g., coat with alumina, then use a dilute base below the nanopore to reopen a nanopore in the alumina, while leaving the rest of the alumina coating intact).

In an aspect, the present disclosure provides a substrate with a membrane comprising at least one nanopore wherein one or more nanoscale electronic elements are aligned with the nanopore. The nanoscale electronic elements can be disposed on or in the membrane containing the nanopore. Thus, the nanoscale electronic element can be fully or partly embedded in the membrane or can be positioned on a surface of the membrane. In an embodiment, the nanopore has aligned nanoscale electronic elements arranged in an array. The nanopore may be configured to provide fluidic communication between opposite sides of the membrane. The nanopore also may be in fluidic communication with an aperture in the substrate. The aperture in the substrate may have the same diameter or a different diameter than the nanopore.

The substrates are formed from or comprise a membrane. The membrane can be a layer of a dielectric, semiconducting, or semimetal material. The membrane also could be a conductor. The membrane comprises one or more of nanopores with nanoscale electronic elements aligned to the nanopores. For example, a membrane made of the dielectric material can have between 1 and 100 nanopores.

The substrate has a region with a space on either side of the dielectric (and adjacent materials), which can be occupied by liquid, such that the dielectric in that region comprises a membrane. For example, such a membrane may have an area of 100 $nm^2$ to 10 $cm^2$, including all values to $nm^2$ and ranges therebetween. For example, the membrane may have an area of 2500 $nm^2$ to 1 $cm^2$. In an embodiment, the nanopores are the only regions in which the solutions above and below the membrane physically contact and/or exchange material or ions with each other.

Dielectric materials such as, for example, silicon nitride, alumina (aluminum oxide), hafnium oxide, tantalum oxide, silicon dioxide, boron nitride, or other semiconducting or 2-d material such as graphene, a metal-dichalcogenide, and the like can be used as the nanopore-containing membrane. Semiconductor or semimetal materials such as, for example, a metal dichalcogenide, graphene, silicon, germanium, gallium arsenide, and the like can be used as the nanopore-containing membrane. For example, the membrane can have a thickness from 0.3 nm to 1,000 nm, including all values to nm and ranges therebetween. In an instance, the membrane has a thickness from 0.3 nm to 500 nm. For example, the substrates and/or membrane can have a size of 100 $nm^2$ to 900 $cm^2$, including all values to $nm^2$ and ranges therebetween. In an instance, the substrates and/or membrane has a size of 2500 $nm^2$ to 900 $cm^2$. In another instance, the substrate and/or membrane has a size of 1 $m^2$ or more.

Suitable substrates are known in the art. Examples of suitable substrates include, but are not limited to, wafers used in semiconductor/microelectronics fabrication processes. For example, the substrate can be silicon (e.g., high resistance (>10 kΩ·cm) silicon) that has a layer of dielectric material disposed thereon. Typical wafers are 0.1-1 mm thick, and are circular with diameters of 25-450 mm, including all values to the mm and ranges therebetween. Other suitable substrates may include insulating substrates such as quartz, fused silica, sapphire, or semiconducting substrates such as doped or undoped silicon, gallium arsenide, silicon carbide, and the like.

The nanoscale electronic elements are aligned to the nanopores of the substrate. The nanoscale electronic elements are electrically conducting. At least a portion of the nanoscale electronic elements are in electrical contact with an electrical circuit and/or the nanopore region. In an embodiment, all of the nanoscale electronic elements are in electrical contact with nanopores. At least a portion of the nanoscale electronic elements may be in physical contact with the nanopore.

The nanoscale electronic element can be formed from materials such as, for example, carbon nanotubes, graphene (e.g., graphene nanoribbons having widths of 5-500 nm, and thicknesses of 1 or more atomic layers), a metallic or semiconducting nanowire (e.g., a silver, gold, platinum, graphene, silicon, or germanium nanowire having a diameter of 5-500 nm), a metal or semiconducting electrode of thicknesses less than 20 nm (e.g., 0.3-50 nm of ALD-deposited or evaporation-deposited metal having one dimension being on the order of microns and one dimension on the order of nm), or a gap between two electrodes. The nanoscale electronic elements can be or function as, for example, a field effect transistor or tunneling junction. An array of nanoscale electronic elements can include more than one of these example materials.

The nanoscale electronic element can conduct electricity or can be made to conduct electricity depending on the electrostatic environment and/or material properties. At least one of the nanoscale electronic elements is capable of conducting electricity. In an example, all of the nanoscale electronic elements are capable of conducting electricity. This nanoscale electronic element can be a conductor, semiconductor, or insulator.

The nanoscale electronic elements are different from surrounding structures with respect to at least one of shape, material composition, electrical conductivity, or chemical bonding. For example, the nanoscale electronic elements are different from the membrane with respect to at least one of these properties.

The nanoscale electronic elements can be carbon nanotubes. For example, the nanotubes have a length of 50 nm to 5 mm, including all values to the nm and ranges therebetween. In an instance, the nanotubes have a length of 200 nm to 100 µm. The nanotubes can have a diameter of 0.7 nm to 5 nm, including all values to the nm and ranges therebetween. For example, the nanotubes are present in an array comprising at least 1 nanotube or 1 to 1000 nanotubes including all values and ranges therebetween, with a density of 1 per 50 nm to 1 per 1 mm or 1 per 50 nm to 1 per 100 µm. In an embodiment, each nanopore has an aligned nanoscale electronic element (e.g., carbon nanotube). The ratio of nanoscale electronic elements (e.g., carbon nanotubes) to nanopores is at least 1:1. In an embodiment, no nanoscale electronic element is aligned to more than one nanopore.

The nanoscale structure to which the nanopore is aligned can be a gap between two electrodes. For example, a pair of metal electrodes having a 0.3-100 nm gap between them (e.g., a break junction, lithographically-defined gap, or stacked electrically-conducting layers separated with an insulator) may be on a membrane, with a nanopore substantially perpendicular to the gap, and self-aligned to the gap. The nanopore could be formed near the gap or could be formed at the gap, such that the nanopore spans the space between the two electrodes, and has an orientation perpendicular to the gap. Thus this geometry defines a tunnel junction-aligned nanopore through which, for example, a biopolymer could be passed for sequential tunneling-current measurements through the biopolymer as it passes through the nanopore.

The nanoscale electronic elements may be exposed to an electron beam or an ion beam with average accelerating voltage of less than 1 kV. Thus, any nanoscale electronic element may not have been exposed to an electron beam or ion beam having an average accelerating voltage greater than 1 kV. In an example, the nanoscale electronic elements are not exposed to an electron beam or ion beam. Electron beams or ion beams with an average accelerating voltage greater than 1 kV can cause damage to the nanoscale electronic elements.

Figure 3:
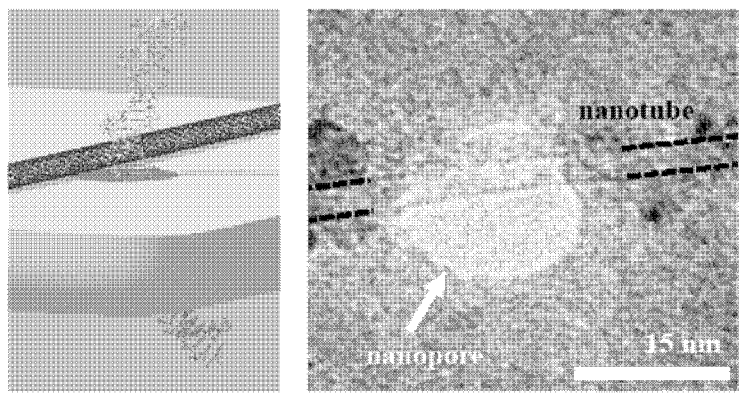
FIG. 3. Example of a carbon nanotube biopolymer sensor aligned to a nanopore using our fabrication method. (a) Schematic of the device configuration with translocating nucleic acid. (b) Transmission electron microscope (TEM) image of an electrically-connected nanotube spanning an approximately 15 nm diameter nanopore.

An exposed surface of the substrate has nanopores. One or more of the nanopores has at least one nanoscale electronic element (e.g., carbon nanotube) aligned with the nanopore. By aligned it is meant that the shortest distance between the edge of the nanoscale electronic element and the edge of the nanopore is less than 50 nm. For example, the shortest distance between the edge of the nanoscale electronic element and the edge of the nanopore can be less than 10 nm or less than 1 nm. In an instance, the nanoscale electronic element is within 0-2 nm of the edge of the nanopore. However, there may be instances where the nanoscale electronic element is within 100 nm of the edge of the nanopore (e.g., detecting large labels or proteins attached to DNA, where the large labels block ionic current, which in turn changes the dielectric (liquid) environment surrounding the nanopore). When an aligned nanoscale electronic element and nanopore are viewed in projection along the nanopore axis, at least one edge of the nanotube can intersect with one edge of the nanopore. For example, the nanotube and nanopore in FIG. 3 are aligned. The nanoscale electronic element may be positioned perpendicular to an axis of the nanopore through the membrane. The nanoscale element also may be positioned parallel to a normal vector defining a plane of a surface of the membrane surrounding the nanopore. For example, see FIGS. 3-5.

A membrane with multiple nanopores may include nanoscale electronic elements aligned to greater than 25% of the nanopores, greater than 50% of the nanopores, greater than 75% of the nanopores, greater than 90% of the nanopores, greater than 95% of the nanopores, or 100% of the nanopores. Of course, a membrane with multiple nanopores also may have other percentages of nanopores with aligned nanoscale electronic elements. For example, a nanoscale electronic element may only be aligned to one of multiple nanopores in a membrane.

The shape of the nanopore can vary. Nanopores can be round, ovoid, square, rectangular, polygonal, or other shapes. The shape of the nanopore also can be irregular. For example, the nanopores can have a depth of 0.3 nm to 1,000 nm or 0.3 nm to 50 nm, including all values to the nm and ranges therebetween. For example, the nanopores can have a width dimension (such as a diameter) of 1 nm to 50 nm, including all values to the nm and ranges therebetween. For example, the width dimension can be 1 nm to 20 nm.

A dimension of the nanoscale electronic element perpendicular to a direction of current flow through the nanoscale electronic element may not exceed 20 nm. In an instance, the dimension of the nanoscale electronic element perpendicular to a direction of current flow through the nanoscale electronic element may not exceed 10 nm.

In an embodiment, the surface of the nanoscale electronic element is chemically modified. For example, the surface of the nanoscale electronic element has one or more functional groups such as carboxyl groups, hydroxyl groups, an amine group, a thiol group, single nucleotides, sequences of nucleotides, an amino acid, a polypeptide, a protein, etc. on at least a portion of an electrode surface. It is expected that sensitivity improvements can be made by chemically modifying the nanotube locally at the nanopore, by functionalization, or by etching away the nanotube at the nanopore to leave a nanotube tunnel junction. This localized chemical modification may be accomplished by, for example, flowing chemicals, gases, and/or plasma through the nanopore from the side of the membrane opposite the side containing the nanotube.

In an aspect, the present invention provides methods for making the nanopore-containing films. Nanopores self-aligned to nanotubes are made by using voltage (positive or negative voltage) applied to nanotubes on the surface of a film to attract ions in an etchant (corresponding to the chemical reaction's rate-limiting step, to locally increase the reaction rate under the nanotube). For example, see the illustration in FIG. 4. In various embodiments, the method comprises, consists of, or consists essentially of the steps described in FIG. 1. In various embodiments, the method comprises, consists of, or consists essentially of the steps described in FIG. 2.

Figure 4:
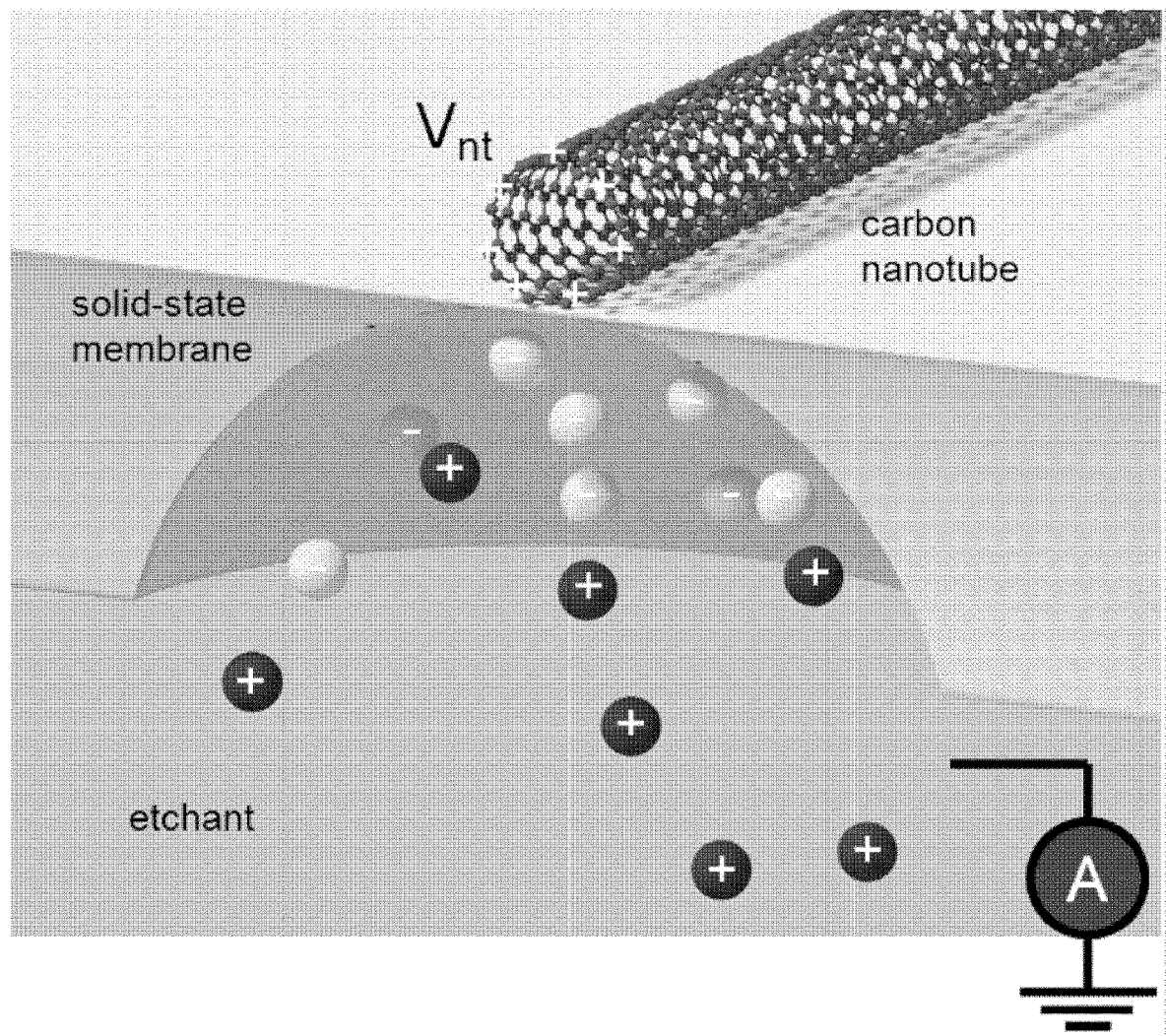
FIG. 4. Schematic of electrochemical self-aligned nanopore formation. Our self-aligned wet-chemical process localizes nanopores to a carbon nanotube, and avoids nanotube damage. A positive voltage applied to the nanotube may attract negative ions in the solution, and locally enhances the etch rate by a factor of approximately 100.
Figure 5:
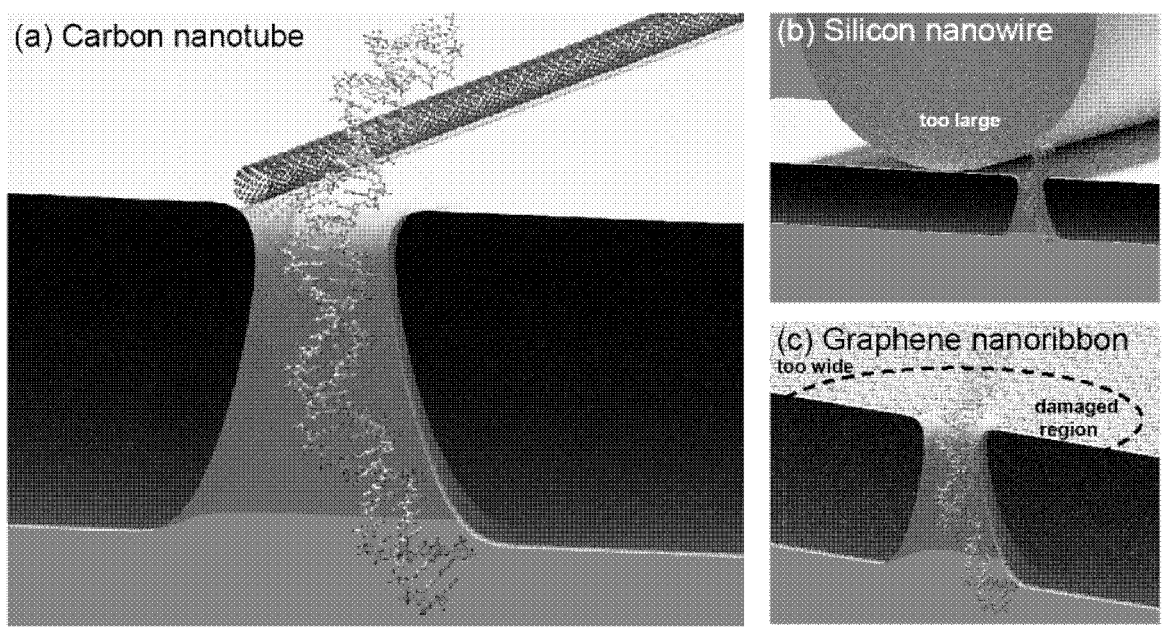
FIG. 5. Schematic of nanotube/nanopore biopolymer measurement. Device cross sections (to scale). Among the options for field-effect-based sequencing of nucleic acid, carbon nanotubes have shape, size, and reliability advantages.

FIG. 4 shows an example in which a voltage is applied to a nanoscale electronic element (here, a carbon nanotube) relative to an electrically-grounded etchant solution. The applied positive voltage attracts negative ions in the solution to the nanotube. In the case where these negative ions are involved in the chemical reaction's rate-limiting step, the etch rate is enhanced beneath the nanotube.

The voltage can enhance or hinder the etching process relative to the etching process in the absence of the applied voltage. In an embodiment, the voltage is chosen such that (for a given membrane thickness) it is high enough to attract negative ions (involved in the reaction rate-limiting step) to the nanotube, enhancing the etch directly across the membrane from the nanotube. If the voltage is too high, negative ions likely block the positive ions (which are not normally rate-limiting, but are still necessary), and the etch rate is enhanced a set distance away from the nanotubes.

A positive pressure can be applied to the solution on one side of the membrane during the etching. For example, a pressure can be applied to fluid on one side of the membrane relative to an opposite side of the membrane. The fluid flows through the nanopore after the nanopore is etched through the membrane. The fluid may not substantially etch the membrane and decreases or halts etching of the membrane. The fluid also can halt or decrease the rate of an increase in the nanopore's diameter or other width dimension.

The following is an example of a method of making a nanopore-containing substrate of this disclosure. Electrically-contacted carbon nanotubes are placed over a thin membrane, which can be silicon nitride, then coated in aluminum oxide, over which a metal gate is deposited. By placing dilute hydrofluoric acid (HF) or phosphoric acid underneath the nitride membrane, and applying a voltage to the nanotube, the rate at which the acid etches the silicon nitride can be greatly enhanced locally under the nanotube, allowing nanopores to be grown in the silicon nitride which are aligned to the nanotube. By measuring current flowing from the top gate electrode to an electrode in the acid, the formation of a nanopore can be detected, and the etch stopped (by turning off the voltage and flushing out the acid) before the nanopore enlarges and before a second nanopore can form. This results in a single nanopore that can be 1-15 nm in diameter (or larger, if desired) and aligned to the nanotube.

Formation of the nanopore can be detected by applying a second voltage to a detection electrode and monitoring current flowing to or from the detection electrode. The detection electrode is separate from the nanoscale electronic element and is positioned outside the etchant. The detection electrode can be fabricated of a metal and can be positioned on a side of the membrane opposite the etchant. For example, a voltage can be applied to a solution on a side of the membrane opposite the etchant using the detection electrode. The detection electrode may be electrically insulated from the nanoscale electronic element by a dielectric or a semiconductor. Other detection techniques, such as using the nanoscale electronic element via ionic detection or FET-based detection also may be used.

In an embodiment, the method for making the films comprises a) forming an array comprising a plurality of nanoscale electronic elements (e.g., carbon nanotubes) on a substrate, where the nanoscale electronic elements are in electrical contact; and b) applying a voltage to the nanoscale electronic element array (e.g., carbon nanotube array) in the presence of an etchant such that nanopores having aligned nanotubes are formed.

Protective layers may be used to keep vulnerable device elements from being damaged by chemical processes (e.g., to potassium hydroxide etching, which is used to etch the silicon wafer from the back, to expose the membrane). The protective layers are substantially free of pin-hole defects. By substantially free of pin-hole defects it is meant that no pin-hole defects are detectable in the protective layer. Pin-hole defects can be detected by, for example, by observing the surface optically after etching with KOH, then removing the protective layer. Where pinholes existed, alumina, silicon dioxide, and/or titanium will have been etched, changing in thickness and thus color. The protective layer may consist of layers of polymer such as Protek B3 and/or layers of metal such as electroplated gold.

The nanoscale electronic elements (e.g., carbon nanotubes) are in contact with a surface of the substrate. The nanoscale electronic elements may be arranged in a predetermined pattern on the substrate. This pattern may be, for example, an array.

In an embodiment, nanotubes, as the nanoscale electronic elements, are arranged such that at least two nanotubes are in contact with each other (e.g., the longest axis of at least two nanotubes for a substantially 90 degree angle) and etching is enhanced in proximity to the contact point.

In an embodiment, temporary interconnects are formed between the electrodes and surface of the substrate (e.g., silicon substrate), to protect the nanotubes from charge build-up and/or voltage/current spikes.

Figure 7:
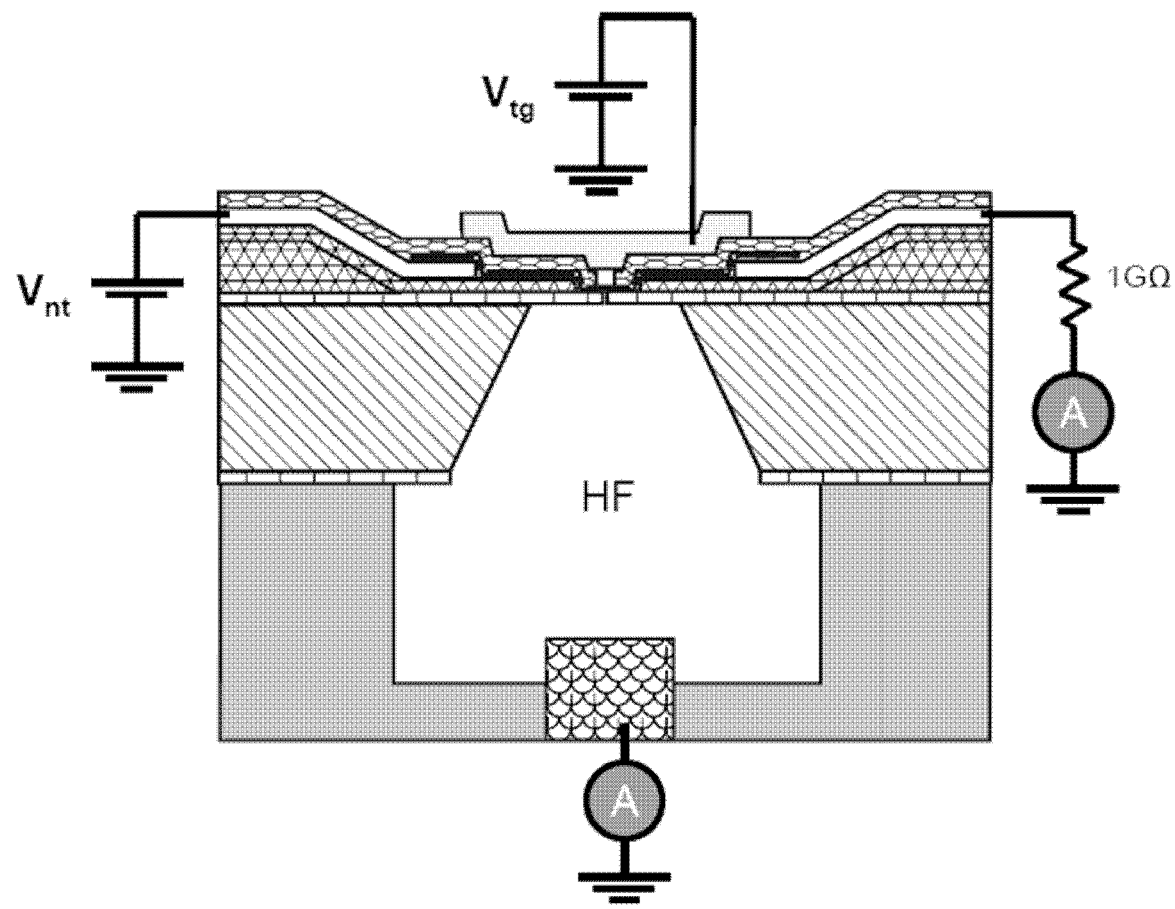
FIG. 7. Example schematic of device configuration for nanopore creation. Voltages are applied to a gold top gate and a platinum nanotube electrode. Currents flowing through the nanotube and through the HF solution (into a copper electrode) are monitored using current preamplifiers. Examples of applied and measured voltages are shown in FIG. 9.

The etchant, which may be a chemical etchant, preferentially etches the substrate in proximity to the nanoscale electronic elements (e.g., carbon nanotubes) when a selected voltage is applied to the nanoscale electronic elements (e.g., carbon nanotubes). Examples of suitable etchants include phosphoric acid, hydrofluoric acid, potassium hydroxide, tetramethylammonium hydroxide, other ion-containing etchants, acids, and bases. The suitability of these etchants will depend on membrane material being used (e.g., for silicon nitride, hydrofluoric acid is a suitable etchant). Example schematics of the etching process and configuration are shown in FIGS. 4 and 7. Space between the nanoscale electronic element and the etchant can be occupied by a portion of the membrane prior to the applying a voltage to cause the etching of the nanopore. The etchant also can contact the nanoscale electronic element while a voltage is applied to the nanoscale electronic element to cause the etching of the nanopore.

Figure 8:
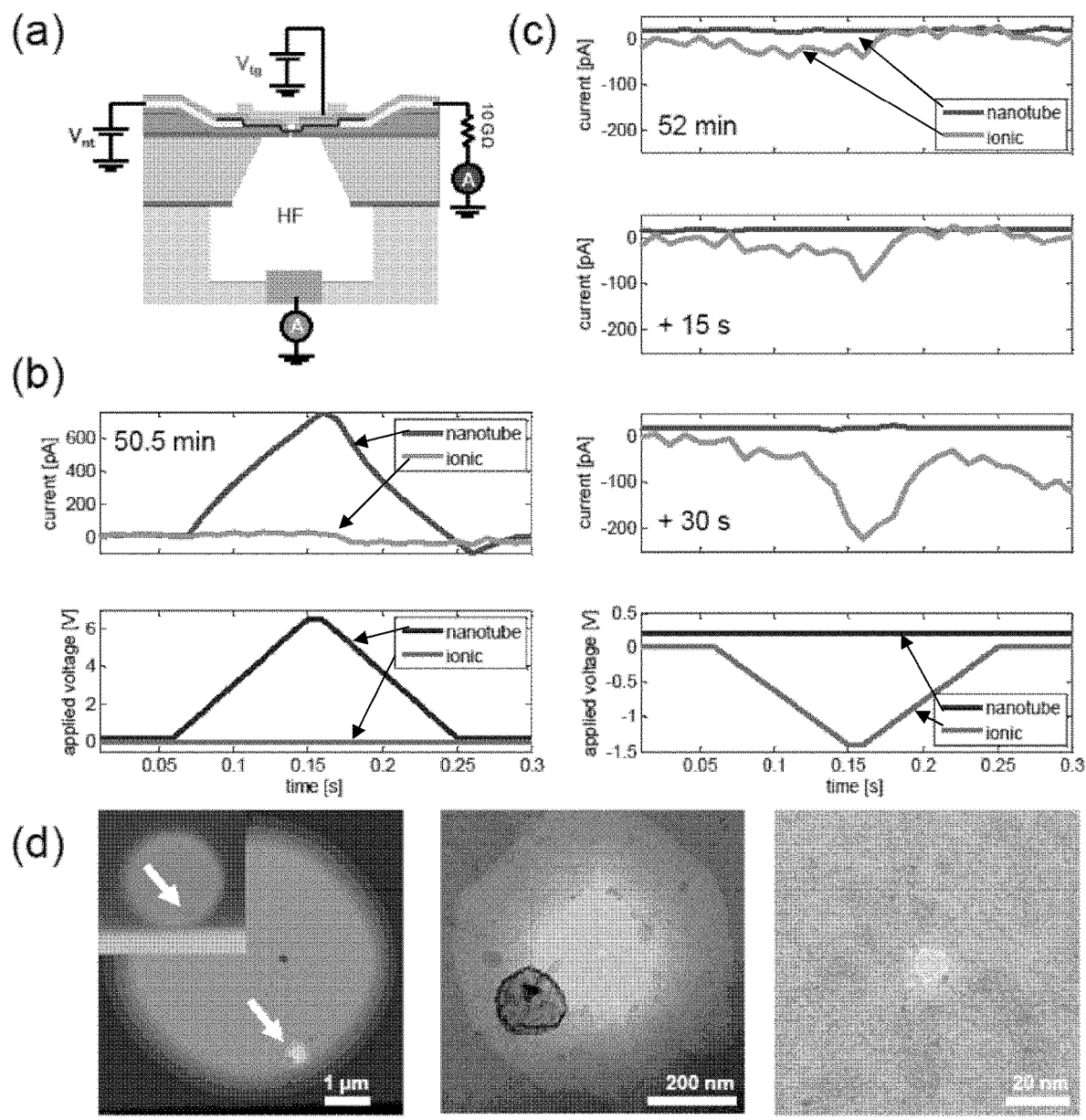
FIG. 8. Example voltage and current traces during nanopore creation. (a) Cross-sectional schematic of device configuration for etching a nanopore. Voltages are applied to a gold top gate and a platinum electrode connected to a nanotube. Currents flowing through the nanotube and through the HF solution (into a copper electrode) are monitored using current preamplifiers. (b) Stage 1 of the etch cycle, in which the voltage on the nanotube is ramped to approximately 6.5 V in approximately 0.25 second. (c) During stage 2 of the etch cycle, a small voltage is applied to the nanotube. Every approximately 15 seconds the top gate is ramped to approximately −1.4 V. The increasingly negative top gate current response show that a nanopore has formed. (d) TEM images reveal an approximately 10 nm nanopore aligned to a nanotube. Inset: optical image showing that the existence of a nanopore is evident.

The voltage applied to the nanoscale electronic element can be applied in a variety of ways. For example, the voltage is applied in pulses, a steady voltage is applied, or a combination of the two. For example, using a 16 nm-thick silicon nitride membrane and 100:1 HF as the etchant, the voltage to the nanotube (relative to the etchant) can be ramped from 0.2V to 10V back to 0.2V in 0.2 s, then held at a constant voltage of 0.2V for 5 minutes, then repeated, until a nanopore has formed. Lower voltages also may be used, though for a given set of parameters (e.g., membrane thickness, etchant type, concentration) the etch often takes longer. For example, 4 V has been used, as shown in FIG. 8. Lower electric fields also can be used (e.g., approximately 10 mV/nm, as in Example 2). The voltage also can be pulsed, ramped, constant, or a combination thereof. Signs and/or magnitudes of the applied voltages can be chosen to minimize damage (e.g., electrochemical attack) to the nanoscale electronic element, enhance the etch rate, and/or enhance electronic detection (e.g., based on electrochemical activity of the nanoscale electronic element and/or of a separate detection electrode, as in FIG. 6, and/or of a separate electrode in contact with the etchant). Larger voltages can be applied to thin the membrane followed by smaller voltages to form a nanopore in the thinned membrane. The voltage that forms the nanopore may be have an opposite sign from the voltage used to detect formation of the nanopore. Other nanopore formation and detection techniques which use lower voltages or lower electric fields are also possible. In general, for a membrane thickness of approximately 15 nm and a 100:1 HF concentration of etchant, "etch pulses" can be 1 millisecond to 5 seconds, and can have a maximum voltage of 6-10V. "Constant voltages" can be 0-0.5V. Higher or lower voltages are possible. The electric field can be 1 mV/nm to 5 V/nm. Time, thickness, concentration, chemical reactivity, and voltage may be related, and can be selected or optimized based on maximizing reliability of alignment and single-pore-formation.

In an embodiment, electrical feedback is used to monitor nanopore formation. Use of electrical feedback may be desirable for small nanopores. For example, nanopores having diameter of 1 nm to 20 nm, including all values to the nm and ranges therebetween, can be made using electrical feedback. A typical procedure is the following. A voltage is applied to a top gate electrode, ramping from 0V to −1.4V to 0V in 0.4 second, then waiting for 15 seconds, then repeating, while electrical current flowing between the top gate and etchant solution is monitored to determine whether a nanopore has formed. Another example is shown in FIG. 8. Other voltages may be applied for other amounts of time. For example, the magnitude of the voltage may be in the range of 1 mV to 10V, though lower magnitude voltages and negative voltages (applied to the nanoscale electrode or detection electrode relative to the solution) can minimize damage to the electrodes. These voltages may be applied for longer or shorter amounts of time. For example, they may be applied for 1 millisecond to 5 seconds, though longer periods of time are possible.

In an instance, etching of the nanopore can be stopped using feedback. The feedback may be, for example, optical or electrical. Optical feedback can be based on at least one of: visible etching of a side of the membrane opposite the etchant; visible accumulation of fluid or formation of crystals at a location of the nanopore; and/or fluorescence activated by formation of the nanopore or interaction of fluorescent dyes with the nanoscale electronic element, the etchant, and/or material that comes into contact with the fluorescent dye due to etching of the nanopore. Electrical feedback can be based on at least one of: changes in current from one side of the membrane to an opposite side of the membrane; changes in current and/or conductance through the nanoscale electronic element (e.g., changes due the field-effect); and/or changes in current flowing between the nanoscale electronic element and the electrode in contact with the etchant.

Etching may be stopped when a magnitude of a current exceeds a threshold, when a rate of change of a current or derivative of current with respect to time exceeds a threshold, or when a shape of a plot of current through the nanoscale electronic element as a function of voltage applied to a detection electrode and/or the electrode in contact with the etchant changes. For example, the root-mean-squared difference between initial and final measured electrical currents at one or more applied voltages may exceed a threshold, such as when the gating characteristics and/or capacitance of the nanoscale electronic element changes. See FIG. 10 for an example of this detection modality. Etching also may be stopped after a designated time. Etching can be stopped by replacing the etchant with a fluid that is less chemically-reactive than the etchant and/or changing the voltage to the nanoscale electronic element. Etching also can be stopped by changing the applied voltage(s) by increasing, decreasing (e.g., decreasing to zero), changing their sign, or by halting a sequence of applied voltages.

Figure 6:
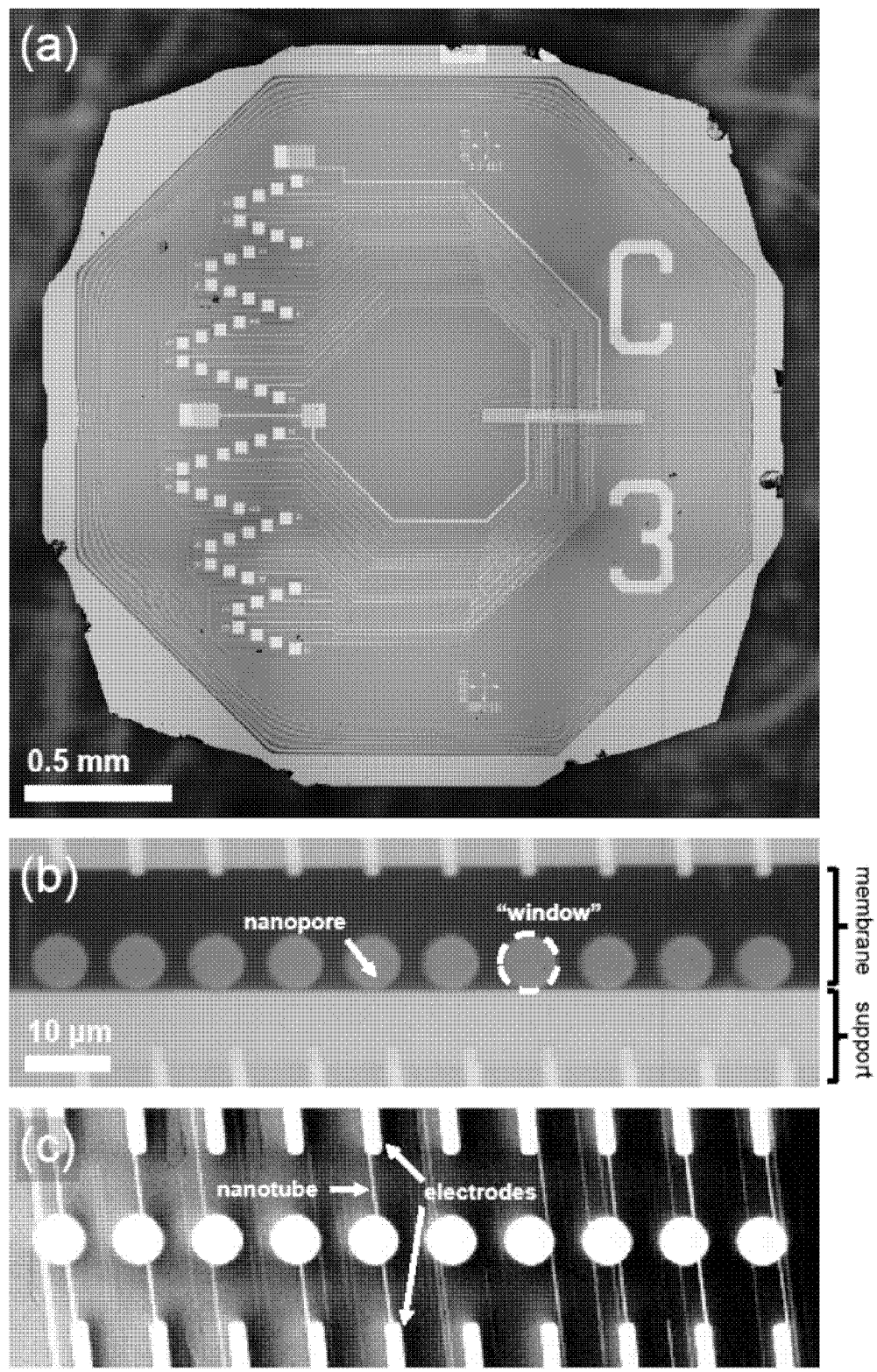
FIG. 6. Microfabricated TEM grid device for nanotube-aligned nanopore fabrication. (a) Optical image of microfabricated TEM grid, with 26 electrode pairs, a gold top gate electrode and a thin window region center-right. (b) Magnified membrane after formation of a nanopore. This is the same device as the one in FIG. 8. The membrane consists of 120 nm of silicon dioxide on 16 nm of nitride; in the "window" regions, the oxide has been removed, leaving only nitride. (c) SEM image of the same region as (b) prior to membrane formation. Nanotubes that are contacting electrodes appear bright (and wide) due to their interaction with the electrons used for imaging.

During the nanopore etch, electrical current flowing between two electrodes on either side of the membrane may be monitored to determine when a nanopore has formed and/or what size it is. This may be accomplished using a metal top-gate patterned onto the device substrate, following the deposition of a coating of dielectric material over the nanoscale electronic element, an example of which is shown in FIG. 6, or by using an electrochemically active electrode in an ion-containing solution (again, with a dielectric layer coating the nanoscale electronic element). Electrode materials that are electrochemically active are used. For example, a copper electrode in HF and a gold electrode on the nanotube-side of the membrane may be used. As another example, a copper electrode in HF may be used, with a silver-chloride electrode in potassium chloride solution on the nanotube side of the membrane. To determine the size of the nanopore, the process may be calibrated by comparing measured electrical conductance at the point when the etch is stopped with the observed nanopore size (e.g. using transmission electron microscopy).

Magnitude and/or sign of the voltage applied during etching can be selected to enhance the etch rate of the membrane proximate to the nanoscale electronic element. For example, the sign and/or magnitude of the voltage can be selected to locally modify the membrane's surface charge density and/or concentration of cations and/or anions in the etchant. The sign and/or magnitude of the voltage also can be selected to overcome the chemical etch reaction's rate-limiting step. The sign and/or magnitude of the voltage also can be selected to attract ions involved in the rate-limiting step toward the nanoscale electronic element. In some instances the etch rate increases non-monotonically with increasing voltage due to a more complex etch mechanism. In such an instance, a voltage may be chosen to optimize etch rate after characterizing the etch rate as a function of applied voltage.

Etching also may be enhanced by increasing concentration of the etchant and/or temperature.

An exemplary nanopore etch in a silicon nitride membrane will be done at room temperature, using hydrofluoric acid (HF), having a concentration of 0.05-2%, with the lower concentrations around 0.2% giving the greatest reliability. The etch can take anywhere from 1 second to 90 minutes, depending on the process parameters. For the sake of reliability, parameters that give a 30 minute etch may be preferred. For a 16 nm-thick silicon nitride membrane, typical parameters will be 0.2% HF, 0.2 second 6-10 V pulses to the nanotube, separated by 2 to 8 minutes at 0 to 0.5V, with −(1 to 1.6) V pulses on the top gate to test whether a nanopore has formed. These parameters may be adjusted if a different membrane thickness or material is used, and/or if the thickness of the dielectric layer between the nanotube and top gate electrode is changed. Typically, this dielectric layer is 10 nm to 460 nm, including all values to the nm and ranges therebetween.

Etching can be localized. Thus, only a single nanopore can be formed or nanopores may only form at nanoscale electronic elements that have voltage applied to them. The etching process can vary between lower voltages than those required for dielectric breakdown. Etching may have a non-monotonic dependence on voltage. For example, localization does not occur using phosphoric acid at 110° C. as the etchant for a 340 nm thick silicon nitride membrane at 25V, but at 12V it does as discussed in Example 2. For dielectric breakdown, the larger the voltage, the greater the breakdown. For the phosphoric acid system, localization does not occur at low temperatures, suggesting that the reactivity of the etchant species affects localization. Dielectric breakdown may be controlled, minimized, or not occur.

One possible mechanism for localized etching is that once a nanopore begins to form in the membrane, it etches at an accelerating speed as the membrane thins. Thus, the first region to etch results in a nanopore before other regions. Other mechanisms for localized etching are possible.

Multiple nanopores also may be formed in the membrane. Each of the nanopores may be aligned to a different nanoscale electronic element. Electrical feedback may be monitored for each of the nanoscale electronic elements. This may use separate detection electrodes, current through the nanoscale electronic elements, and/or current between the nanoscale electronic element and the etchant. Etching can be stopped at individual nanopores by changing the voltage to the one of the plurality of nanoscale electronic elements, or stopped by a self-limiting method such as with the use of an inert fluid that is forced through any formed nanopores by a transmembrane pressure difference.

Figure 13:
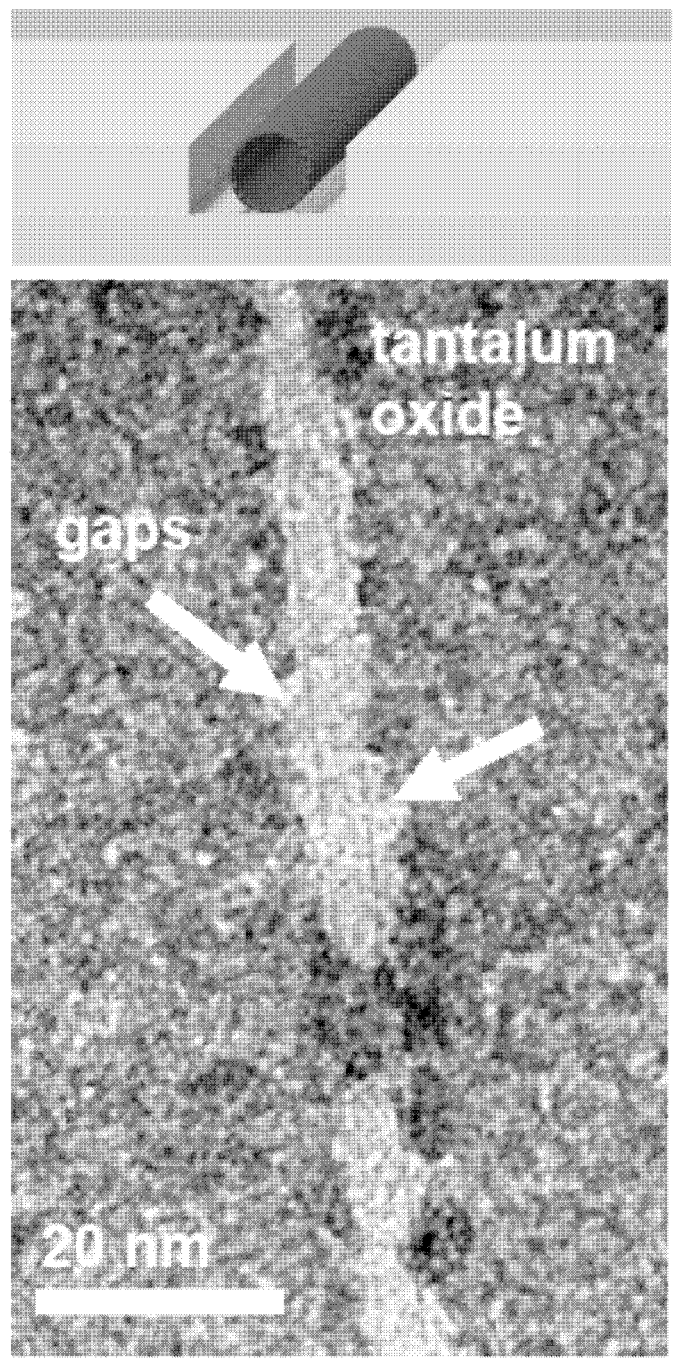
FIG. 13. One approach to reducing nanopore size is to coat the membrane surface with a material that selectively avoids the nanotube (here, tantalum oxide), leading to <5 nm gaps on either side of the nanotube. Upon nanopore formation, these should define the edges of a much smaller nanopore.

To further reduce the size of nanopores and the precision with which they are localized to the nanoscale electronic element, it is expected that coating the surface with a thin material that selectively coats membrane material, but not the nanoscale electronic element, will enable the formation of nanopores that are 1-5 nm in diameter. For example, for carbon nanotubes on a silicon nitride membrane, atomic layer deposition can be used to deposit 0.5-5 nm of tantalum oxide, which selectively coats the silicon nitride, but at these thicknesses, does not coat a carbon nanotube, leaving a gap on either side of the nanotube, as shown in FIG. 13. During the nanopore etch, since tantalum oxide is less reactive than silicon nitride, the gap defines a thinner nanopore adjacent to the nanotube.

During etching of the nanopore, an average electric field along a shortest distance between any region of the nanoscale electronic element disposed on or in the membrane and the etchant may be less than 0.1 V/nm.

Damage to the nanoscale electronic elements can be minimized or eliminated during etching. Damage can be defined as one or more of an irreversible decrease in conductivity of a nanoscale electronic element, an increase in electrical noise measured as a temporal variation in a nanoscale electronic element's current at a given voltage (e.g., the power spectral density of current noise), changes to the structure and/or chemical bonds in a nanoscale electronic element, or other metrics of damage.

In an instance, voltage is applied in a particular manner. A first voltage is applied to the nanoscale electronic element relative to the electrode in contact with the etchant whereby etching of the membrane is induced. A second voltage is applied to the nanoscale electronic element relative to the electrode in contact with the etchant. The second voltage induces an electric field of less than 0.1 V/nm across the membrane. These voltages may be repeated in sequence. Current from the etchant to the nanoscale electronic element is monitored while the second voltage is applied. An increase in the current from the etchant to the nanoscale electronic element is detected. Then the first voltage and the second voltage are removed when the nanopore is formed.

In an aspect, the present disclosure provides methods for using the nanopore-containing membrane. For example, the nanopore-containing membrane can be used for detecting and/or sequencing a biopolymer. A biopolymer may be, for example, a nucleic acid (e.g., DNA or RNA), other polymers (e.g., polypeptides, proteins, and the like), sensing molecules attached to nucleic acids, or other polymers (e.g., short double stranded segments attached to single-stranded nucleic acids, proteins or other epigenetic information attached to nucleic acids, labels, and the like). The nanopore-containing membrane can be used for high speed, low cost sequencing and medical or biological diagnostics (e.g., using nucleic acid "barcodes" to identify microorganism genomes).

Nucleic acid means a plurality of nucleotides. This may be, for example, DNA or RNA. The nucleic acid may be natural or non-natural. The nucleic acid may be single-stranded or double-stranded. The nucleic acid may be approximately 1,000-50,000 bpr long. DNA as short as 11 nucleotides has been detected.

The nanopore-containing films can be used to detect biopolymers and/or sequence biopolymers, such as DNA.

Figure 14:
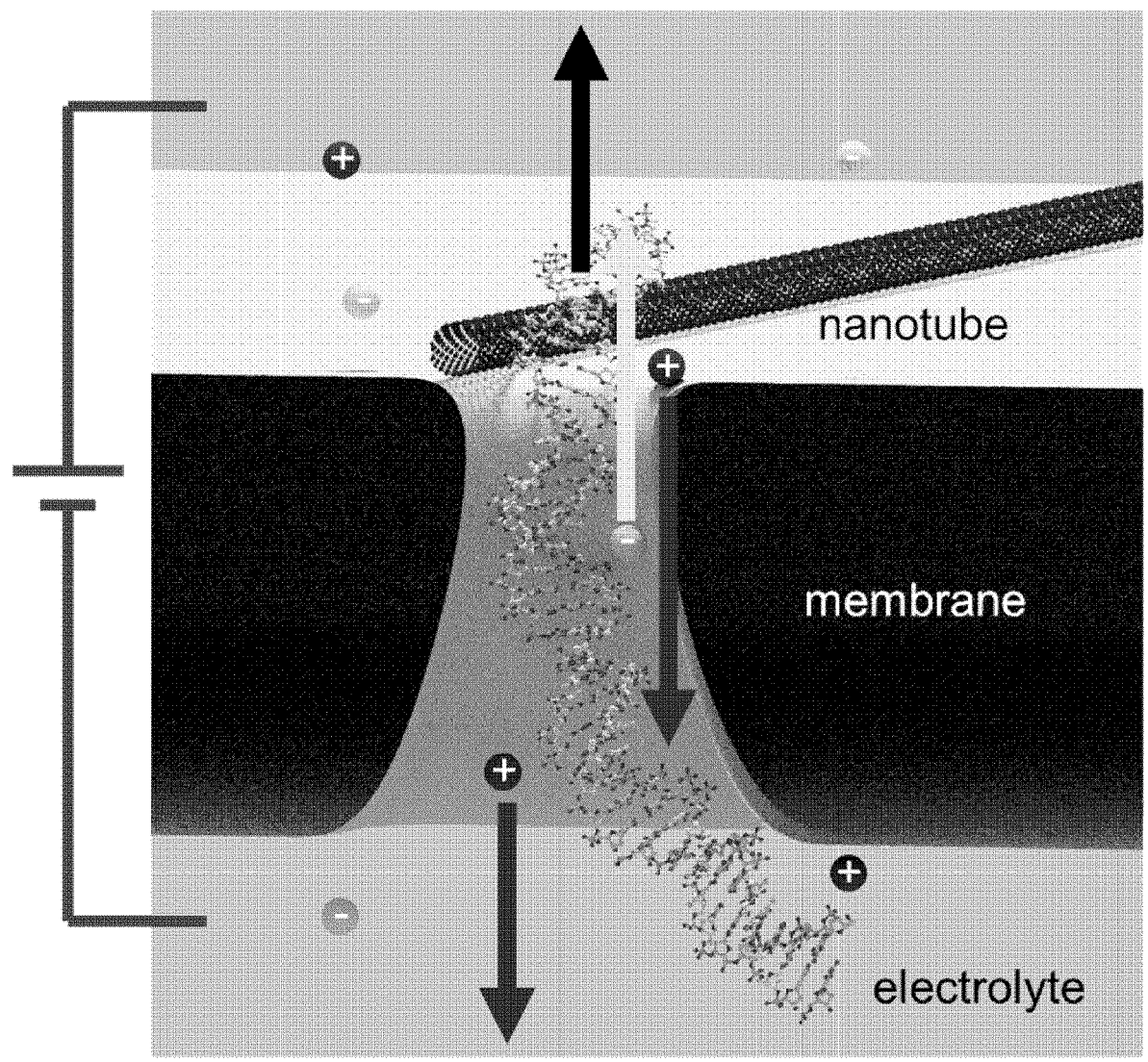
FIG. 14. Voltage applied to the solution above relative to the solution below the membrane drives ions and nucleic acid through the nanopore. A separate voltage applied to either side of the nanotube (not shown) can be used to drive an electrical current through the nanotube. This current will vary depending on the proximity of ions and nucleic acid to the nanotube.
Figure 15:
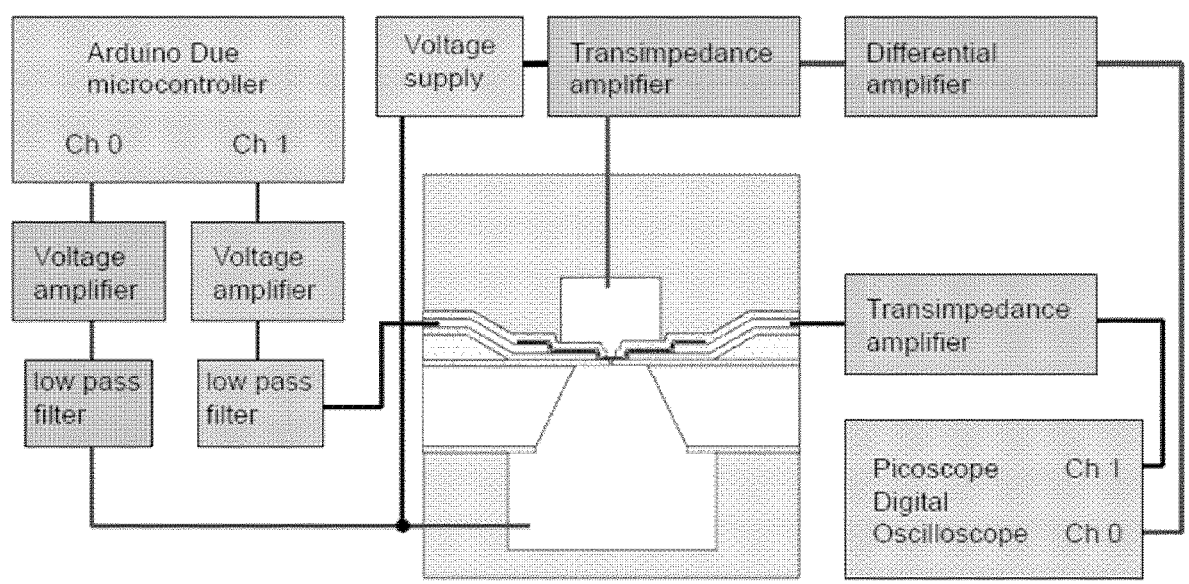
FIG. 15. Nucleic acid translocation measurement setup. Voltages are applied to one side of the nanotube and currents measured at the other side. Voltages are applied to the ionic solution containing nucleic acid in the microfluidic channel beneath the device, and currents flowing through the nanopore are measured at the microfluidic channel above the device. An additional voltage supply is used to allow the solution potential (top and bottom) to be varied relative to the nanotube.

With nanopores aligned to nanoscale electronic element(s), detection of labels or monomer units (e.g., nucleotides in DNA) may occur according to their proximity to the nanoscale electronic element(s) and/or linear charge density by the field-effect in which the electrical conductance of the nanoscale electronic element(s) varies in response to changes in its adjacent charge or dielectric environment. The field-effect based biopolymer detection mode is separate from the electrophoretic biopolymer driving mechanism. In this detection mode, a voltage applied to the ionic solution on one side of the nanopore-containing film relative to the solution on the other side drives a biopolymer through the nanopore. A transmembrane pressure difference may also be used to drive fluid and/or the biopolymer through the nanopore. Simultaneously, and independently, a second voltage is applied to one side of the aligned nanoscale electronic element (e.g., carbon nanotube), and the current through the nanoscale electronic element is monitored. It is expected that single-stranded nucleic acid and double-stranded nucleic acid can be distinguished from each other. In the methods of detecting nucleic acids and/or sequencing nucleic acids, ionic currents through the nanopore and electrical currents through the nanoscale electronic element can be generated and monitored simultaneously. Thus, it is expected that these two methods can be used to detect and/or sequence nucleic acids simultaneously. An example schematic of ions and nucleic acid being driven through the nanopore and detected while a nanoscale electronic element measures the nucleic acid is shown in FIG. 14 Another example showing a possible configuration for the drive and detection electronics is shown in FIG. 15. A biopolymer detection and/or sequencing system may be included, which can have a power source or a controller. The controller can include a processor, an electronic storage device in electronic communication with the processor, and a communication port in electronic communication with the processor. The processor can receive readings from the nanoscale electronic element(s), electrical circuit in electrical contact with the nanoscale electronic element(s), and/or the substrate, such as through an electronic connection. Using these readings, the processor can be configured to detect and/or sequence biopolymers, such as nucleic acids. A data recording system can be electronically connected with the biopolymer detection and/or sequencing system. The data recording system can include memory and may be part of or separate from the controller.

The present disclosure is expected to provide a cheaper and faster method of sequencing biopolymers than currently exists, potentially without the need for amplification or labeling of biopolymers, and potentially with longer read lengths than those currently available. Avoiding the need for amplification or labeling saves time and resources. Obtaining longer read lengths enables the sequencing of long sections of repeating sequences, which are difficult or impossible to obtain with methods where a biopolymer is broken into short segments and then reconstructed statistically. Additionally, a field-effect readout has essentially no limitation to the number of nanopores (and, thus, sequencing elements) per microfluidic channel through which fluid flows to or from the nanopore(s), in contrast to transmembrane ionic-current-based sequencing, in which the signal due to current flowing through separate nanopores in a single membrane separating two bodies of liquid cannot easily be distinguished.

The methods of biopolymer detection/sequencing of this disclosure provide multiple unique features. A biopolymer, such as a nucleic acid, is detected and/or sequenced using a carbon nanotube or other nanoscale electronic element. A nanopore constrains the biopolymer to move linearly past the nanotube or other nanoscale electronic element in a direction perpendicular to the nanotube or other nanoscale electronic element, in close proximity to the nanotube or other nanoscale electronic element. For example, the nanotube's diameter can be <1 nm, DNA spacing is 0.34 nm. By averaging data from a few biopolymer translocation events with similar translocation rates, correlation between known nucleotide sequence and measured nanotube current is obtained. It is expected that a biopolymer with unknown sequence can then be sequenced based on this correlation/calibration. In contrast to ionic-current based measurements, nanotube measurements can be made at >10 MHz bandwidth due to significantly reduced capacitance, and high-mobility electrical conduction.

The speed of biopolymer translocation (and thus number of data points per nucleotide), which is controlled by the transmembrane voltage, is almost entirely decoupled from the detection mechanism. One limitation to ionic current based detection is that the signal increases with increasing transmembrane voltage, but that also increases the translocation rate, which reduces the number of data points per nucleotide and cancels out the increase in signal size.

The device sensitivity can be tuned by varying the ionic solution voltage relative to the nanotube, which tunes its Fermi level and thus its transconductance, a voltage applied to the nanotube relative to the solution is expected to affect the biopolymer translocation rate and/or the proximity and/or the orientation of the biopolymer relative to the nanotube during translocation.

The following is an example of a method of using the nanopore-containing substrates of this disclosure to detect/sequence DNA. The top gate electrode is removed after nanopore formation and detection, and the device cleaned and dried. Potassium chloride is placed on either side of the nanopore-containing nitride membrane. DNA can be detected by applying a voltage using a set of silver/silver chloride electrodes in the solutions on top and bottom, and measuring the current flowing through the nanopore. A bias voltage can also be applied to the nanotube with a separate set of electrodes, and the nanotube conductivity monitored. A third bias between the ionic-current electrode pair and the nanotube electrode pair can be used to tune the Fermi level of the nanotube to adjust its sensitivity. DNA in KCl/buffer can be flowed into microfluidic channels over the top and bottom of the device membrane, and simultaneous (or isolated) measurements of the nanotube conductance and nanopore conductance can be made. When DNA is proximate the nanotube, it is locally gated through the field effect, and its conductance changes in correspondence with the DNA's proximity. The nanopore forces the DNA to pass linearly past the nanotube in a direction perpendicular to the nanotube.

In an embodiment, the method of using the nanopore-containing substrates to detect/sequence a biopolymer comprises contacting a substrate of the present disclosure with sample comprising a biopolymer, such as DNA, in solution; and applying a voltage to one side of the membrane relative to the other, while measuring the ionic current through the nanopore produced by this voltage. Simultaneously, a voltage is applied to a nanopore-aligned nanoscale electronic element, and the current passing through the nanoscale electronic element is monitored. For example, 0.1-100 µM DNA in KCl/buffer solution may be introduced to one side of the membrane, and KCl/buffer or water may be introduced to the other side, and a positive voltage from 50 mV to 3V applied to the non-DNA side relative to the DNA side. This will electrophoretically drive the DNA through the nanopore. Ionic current flowing in parallel through the nanopore may be monitored, which will typically decrease when DNA is passing through the nanopore. At the same time, a voltage is applied to one side of the nanotube, and current flowing through the nanotube is monitored. As DNA passes by the nanotube, the conductance of the nanotube (and thus the current flowing through it) will be modified by the charge, and/or proximity of the DNA and/or ions in solution. The detected signals for known DNA sequences may be used to develop or train an algorithm (e.g., a machine learning algorithm, linear or logistic regression, etc.) to determine DNA sequence in DNA for which the sequence is unknown.

In an aspect, the present disclosure provides devices comprising the nanopore-containing films of the present disclosure. For example, the device can be used to detect/sequence a biopolymer.

A device of the present disclosure configured to detect/sequence biopolymer provides multiple unique features. The device used in the biopolymer detection/sequencing methods can be configured to have low capacitance, which provides a desirable signal-to-noise ratio at high measurement bandwidth. This can be achieved by using thin electrodes, thick low-k dielectric separating electrodes from substrate and upper microfluidic channels from lower ones, a highly resistive silicon substrate, narrow microfluidic channels, a dielectric coating over the electrodes and nanotube, a custom-built transimpedance amplifier with attached electrical probe to measure current through the nanotube and nanopore. Noise can also be reduced by running the entire system off batteries and electronics. Most of these electronics and batteries can be housed in metal boxes to act as Faraday cages, further reducing noise. Data can be recorded with a bandwidth of >2 MHz.

In an embodiment, the device has the configuration shown in FIG. 1-3, 5-6, or 15. Necessary components include a membrane separating two regions that can contain liquid. A nanopore in such a membrane that is aligned to an electrically-conducting nanostructure connected to an electrical circuit; a substrate to support such a membrane. Other features may be important for the fabrication process (e.g., material choices), to give desirable measurement characteristics (e.g., thick dielectric layers beneath the metal electrodes for high bandwidth), or to give the ability to characterize or study the device and fabrication process (e.g., 3 mm device size useful for transmission electron microscopy to view the nanopores).

The following examples are presented to illustrate the present invention. They are not intended to be limiting in any manner.

Example 1

In this example, a nanopore in a silicon nitride membrane is self-aligned to a carbon nanotube, and DNA is driven through the nanopore and detected using ionic current through the nanopore, or by using electrical current through the nanotube. The device was fabricated using the process outlined in FIG. 1. FIG. 6 shows the resulting device. The device has 26 pairs of electrodes, between which are carbon nanotubes. A gold top gate was used to enable electrical feedback during the nanopore etch. Later in the process this was removed, revealing the membrane, thinned square window regions, and an etched nanopore in one of the thin regions, shown in FIG. 6 (*b*). Although the nanopore is too small to be seen optically, the dielectric layer that was between the top gate and the nanotube also gets etched to a size of approximately 1 µm, making it visible as a dark patch.

Figure 9:
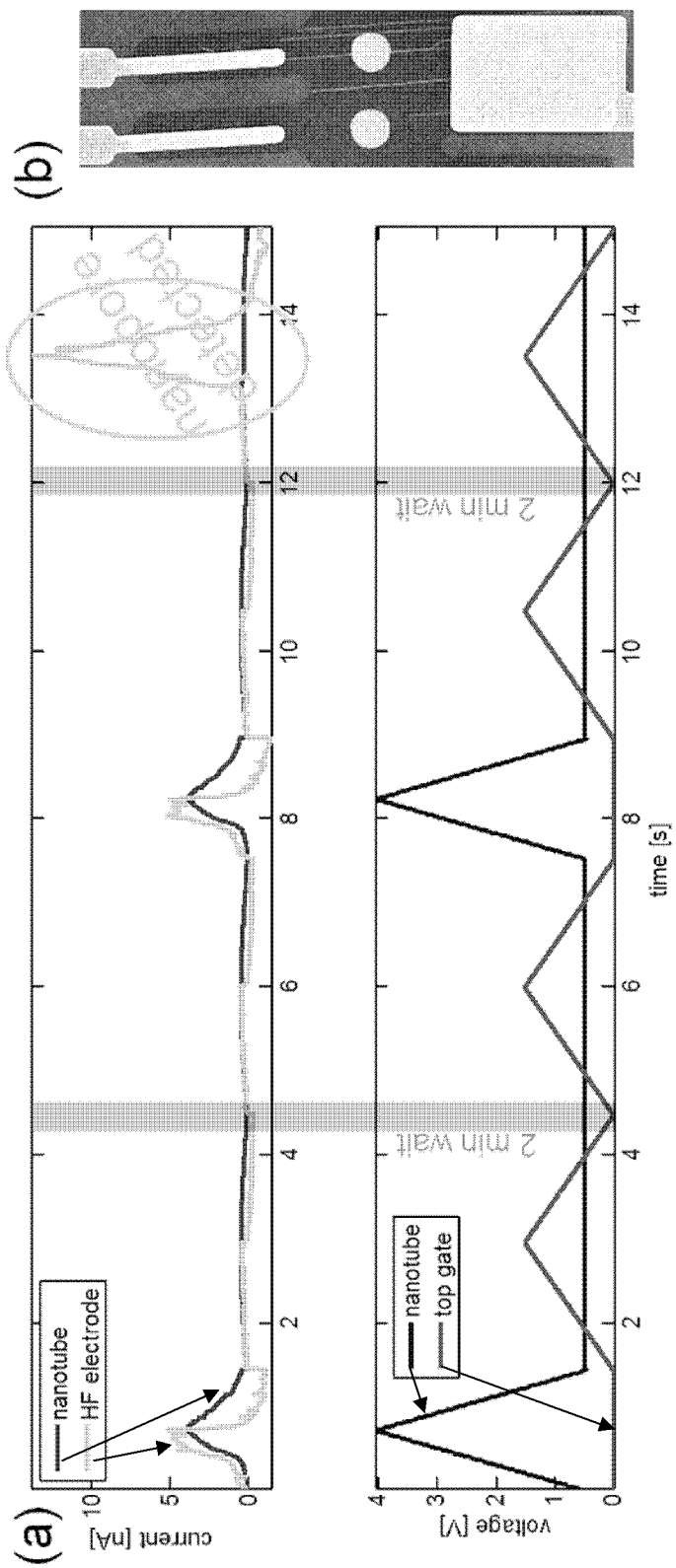
FIG. 9. Nanopore formation and detection. (a) A series of voltage ramps are applied to a nanotube to self-align a nanopore in a silicon nitride membrane to the nanotube. Sweeps of a top gate electrode are used to probe whether a nanopore has formed. Once a nanopore forms, this is detected as an electrical current from the top gate electrode to the electrode in the HF solution. (b) SEM image of the device used in (a). Platinum electrodes connect to a nanotube that spans a plasma-thinned region of the nitride membrane (lighter circle).

A nanopore was formed such that it is self-aligned to a nanotube on top of a membrane by flowing dilute 0.5% hydrofluoric acid (HF) on the underside of the membrane, while using electrical feedback to determine when a nanopore has formed and to then stopping the etch by setting voltages to zero, and flushing out the HF, as described elsewhere in this disclosure. A diagram of the device configuration during a nanopore etch is shown in FIG. 7, and an example of the voltages applied and currents measured for one such device is shown in FIG. 9.

Figure 12:
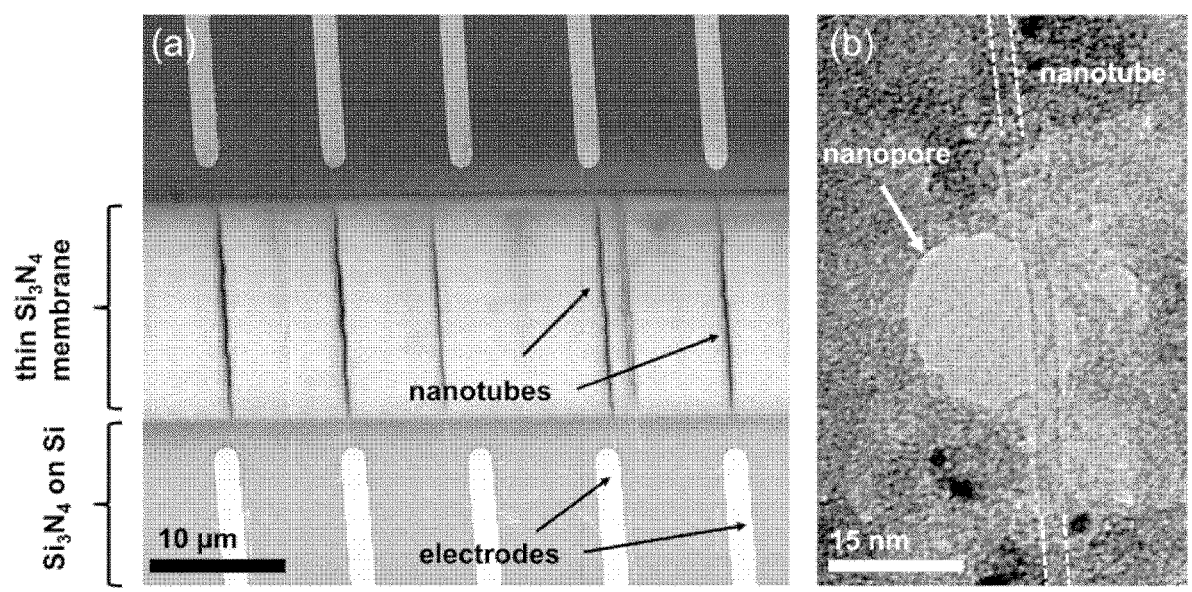
FIG. 12. Device images. (a) Arrays of carbon nanotubes span a thin membrane between pairs of electrodes, as imaged by scanning electron microscope (SEM). (b) A transmission electron microscope (TEM) image of an approximately 15 nm nanopore aligned to an approximately 4 nm diameter nanotube.

FIG. 12 (a) shows a scanning electron microscope image of a device before the nanopore etch had occurred, with carbon nanotubes spanning a thin membrane and connected on either side to metal electrodes. After a nanopore was etched, it was viewed by transmission electron microscopy, and in (b) the nanopore is seen to be aligned to the nanotube.

To perform DNA detection and/or sequencing measurements, the device was connected to a set of electronic components, as shown in FIG. 15. Microfluidic channels were attached to the top and bottom of the device. 100 µM DNA in 2M KCl solution was flowed through the bottom channel, and 2M KCl (without DNA) is flowed through the top channel. Electrical contact to these solutions was made using silver/silver-chloride electrodes (not shown). A voltage from −50 mV to −2 V was applied to the lower solution and the current flowing through the nanopore was measured in the upper solution. A voltage from 5 mV to 200 mV was applied to one side of the nanotube, via its metal contacts, and the current flowing through the nanotube was detected on the other side. Data were recorded at 8 megasamples per second using a digital oscilloscope, and transferred to a computer.

Figure 16:
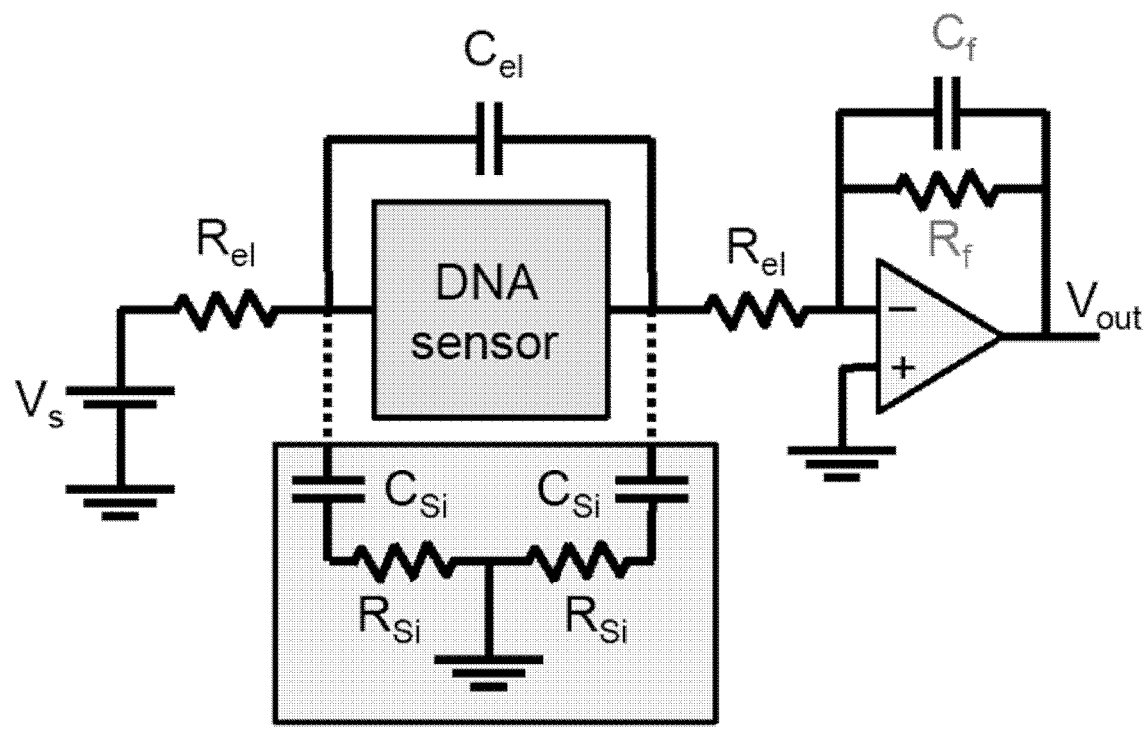
FIG. 16. Nucleic acid sensing circuit. Circuit diagram for nanotube- or ionic current-based nucleic acid sensing. Resistors and parasitic capacitances for electrodes/electrolyte (el), transimpedance amplifier feedback (f), silicon wafer (Si), are indicated.

The device measurement apparatus is in an acrylic microfluidic device holder with three electrical probes, two of which have built-in preamplifier circuits. An example of a transimpedance amplifier circuit used to measure changes in current in the nanotube or ionic signals is shown in FIG. 16. Batteries supply power to these amplifiers, and the measurement setup is on the base of a metal box, which can be closed, acting as a Faraday cage that reduces electrical noise.

Figure 17:
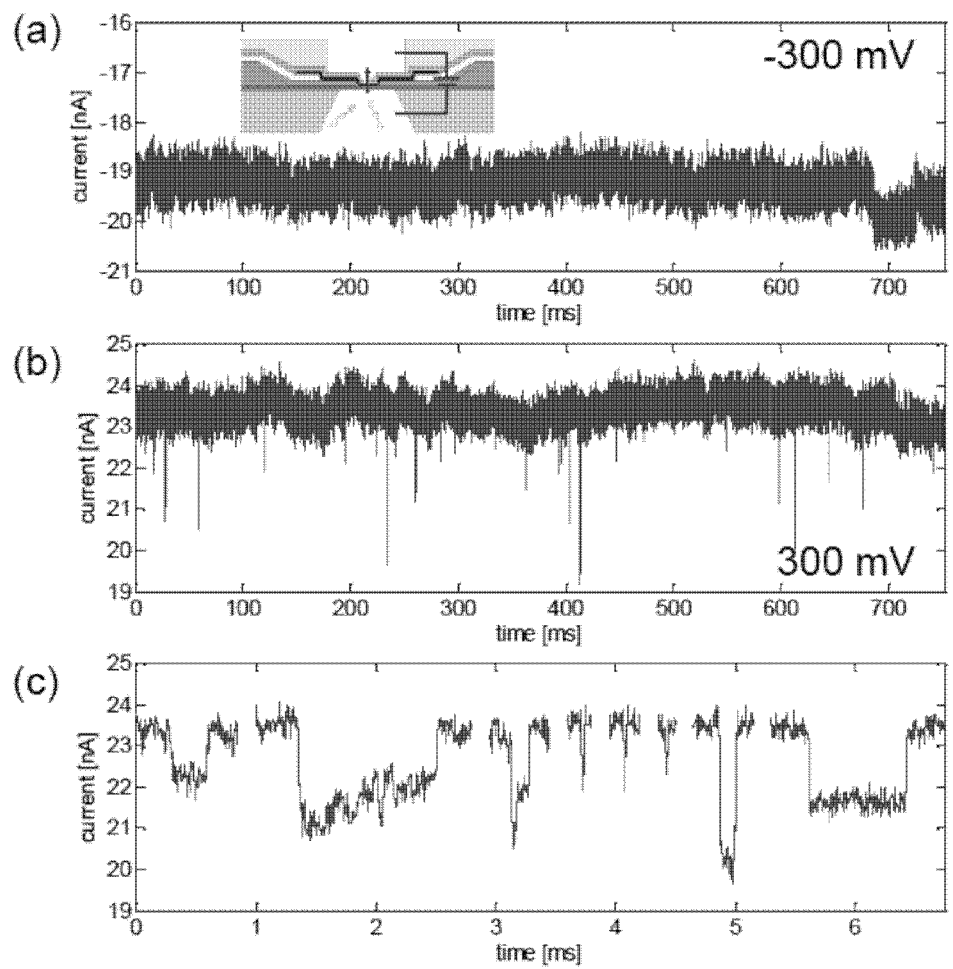
FIG. 17. Ionic detection of 30 consecutive adenine (dA) nucleotides in single-stranded DNA, ssDNA ($dA_{30}$), translocating through a nanopore. (a) Under a negative bias, no nucleic acid translocates the nanopore. (b) When the bias is positive, nucleic acid is driven through the nanopore by electrophoresis, temporarily reducing the current as it partially occludes the nanopore. (c) A magnified view of the first eight DNA translocation events from (b).
Figure 18:
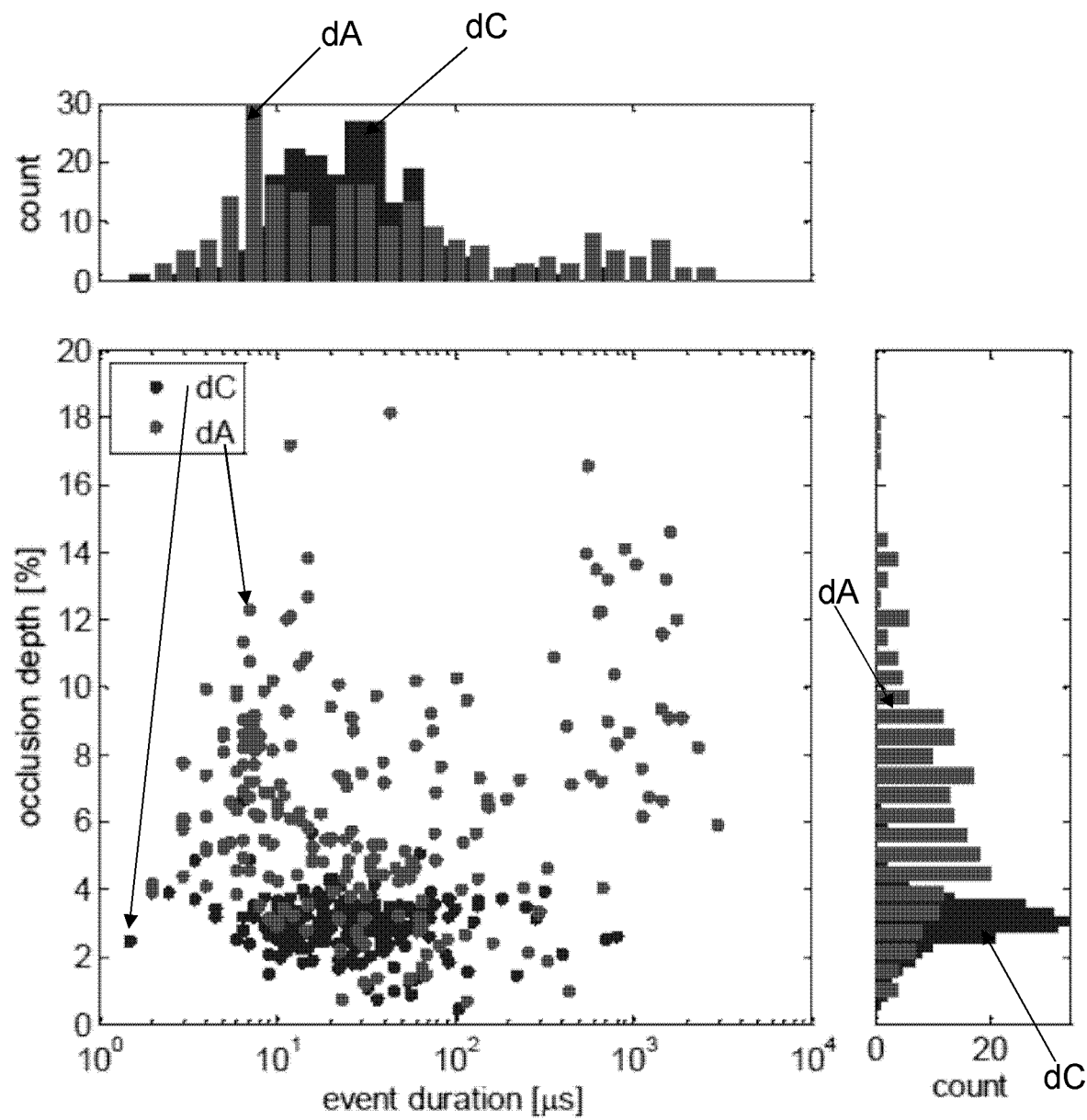
FIG. 18. Distribution of current and duration of translocation events for ssDNA consisting of 30 consecutive cytosine (dC) or adenine (dA) nucleotides. The histograms show that while the dC and dA event durations are very similar, the distributions of occlusion depths are significantly different. The secondary population of dA events with approximately 1 ms duration are likely 3 kbp DNA not fully flushed from a prior measurement.

DNA can be detected ionically by the devices, as shown in FIG. 17. Short, single stranded DNA (11 or 30 nucleotides) was flowed into the lower microfluidic channel. A voltage of 300 mV was applied across the membrane, and the current flowing through the nanopore was recorded. When DNA passes through the nanopore, it partially blocks the ions flowing through the nanopore, leading to dips in the nanopore conductance. Thus each of the downward spikes in the ionic current corresponds to the detection of a single molecule of 11-nucleotide single-stranded DNA (ssDNA) passing through the nanopore in 10-100 µs. When this measurement process is repeated for 30 nucleotide-long single-stranded DNA, it was found that the depth of the dips in the ionic current were different for different sets of DNA, as shown in FIG. 18. Ionic current nanopore measurements can distinguish between ssDNA consisting of 30 consecutive adenine bases (dA) and ssDNA consisting of 30 consecutive cytosine bases (dC).

Figure 20:
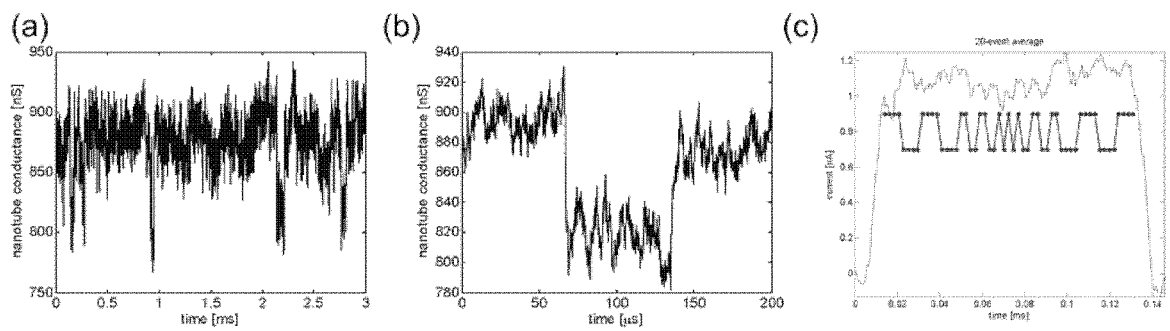
FIG. 20. Nanotube DNA translocation measurements. (a) Nanotube conductance. As 52 nucleotide ssDNA translocates through the nanopore, dips in the conductance of the nanotube are detected. (b) A short time period from (a) showing one approximately 70 µs is translocation event. (c) Averaging 20 such events (black), plotted inverted, suggests that DNA sequence information may be present. As a comparison, plotted in red is the known DNA sequence of the translocating DNA where larger values represent adenine (A), and lower values represent cytosine (C).

Changes in electric current through the nanotube as DNA translocates through the nanopore were also be used to detect DNA. FIGS. 20 (a) and (b) shows the nanotube conductance as DNA passes through the nanopore. Dips in the nanotube current correspond to 52-nucleotide ssDNA passing through the nanopore, next to the aligned nanotube, in 20-200 µs. Averaging a set of similar-length events (approximately 140 µs), and comparing the resulting trace to the known sequence of the DNA being passed through the nanopore, FIG. 20 (c), an indication that sequence information may be obtainable using these relatively high-speed nanotube-based DNA nanopore translocation measurements was seen. Both this averaged measurement and the known sequence have mirror symmetry, and toward the center of the trace, current fluctuations are shallow and rapid, while towards the edge they wider are more pronounced, as expected for the known sequence.

Figure 19:
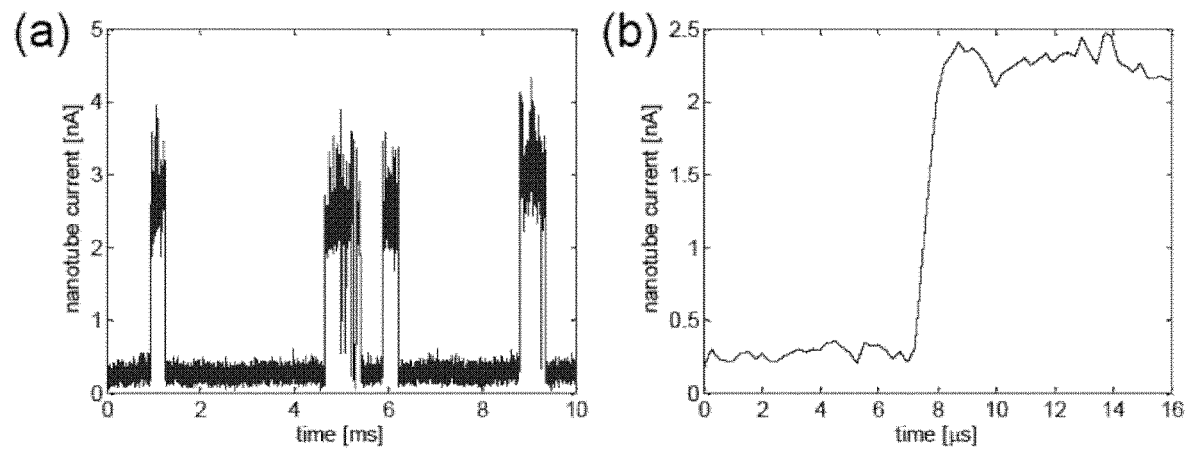
FIG. 19. Nanotube speed and sensitivity test. (a) Single-electron fluctuations in the nearby dielectric are detected as binary changes in nanotube current. (b) The nanotube (and amplifying electronics) responds to these charge fluctuations in less than a microsecond, with a signal-to-noise ratio of 40.

As another test of the speed and sensitivity of our nanotube-based sensors and electronics, the response of one of these nanotubes to single-electron fluctuations in the nearby dielectric materials was observed. It was found in this example, the nanotube and electronics responded to these events with a signal to noise ratio of 30, in less than 1 µs, as shown in FIG. 19. This is within the range of speed and sensitivity where DNA sequencing is expected to be carried out.

Example 2

In this example, nanopores in a silicon nitride membrane are self-aligned to carbon nanotubes using hot phosphoric acid as the etchant. This example demonstrates that techniques disclosed herein can be successfully applied using different etchants, different membrane thicknesses, and lower electric fields than those in Example 1. Furthermore, the nanotube-localized nanopore etch rate can have a non-monotonic dependence on voltage. This is consistent with the picture that the voltage on the nanotube locally induces a change in the concentration of positive ions relative to negative ions in the etchant. The reaction occurs at the greatest rate when the relative concentration reaches a particular optimal ratio. The voltage may be tuned such that this optimal ratio occurs at a location that is the shortest distance between the nanotube and the etchant. In this phosphoric acid etch system, the etch rate also depends heavily on temperature, and does not occur at an appreciable rate at temperatures below 50° C.

FIG. 4 shows a schematic of the proposed nanopore-etch localization procedure. A voltage is applied to a nanoscale electrode (here, a carbon nanotube) relative to an electrically-grounded etchant solution. The applied positive voltage attracts negative ions in the solution to the nanotube. In the case where these negative ions are involved in the chemical reaction's rate-limiting step, the etch rate is enhanced beneath the nanotube.

Figure 2:
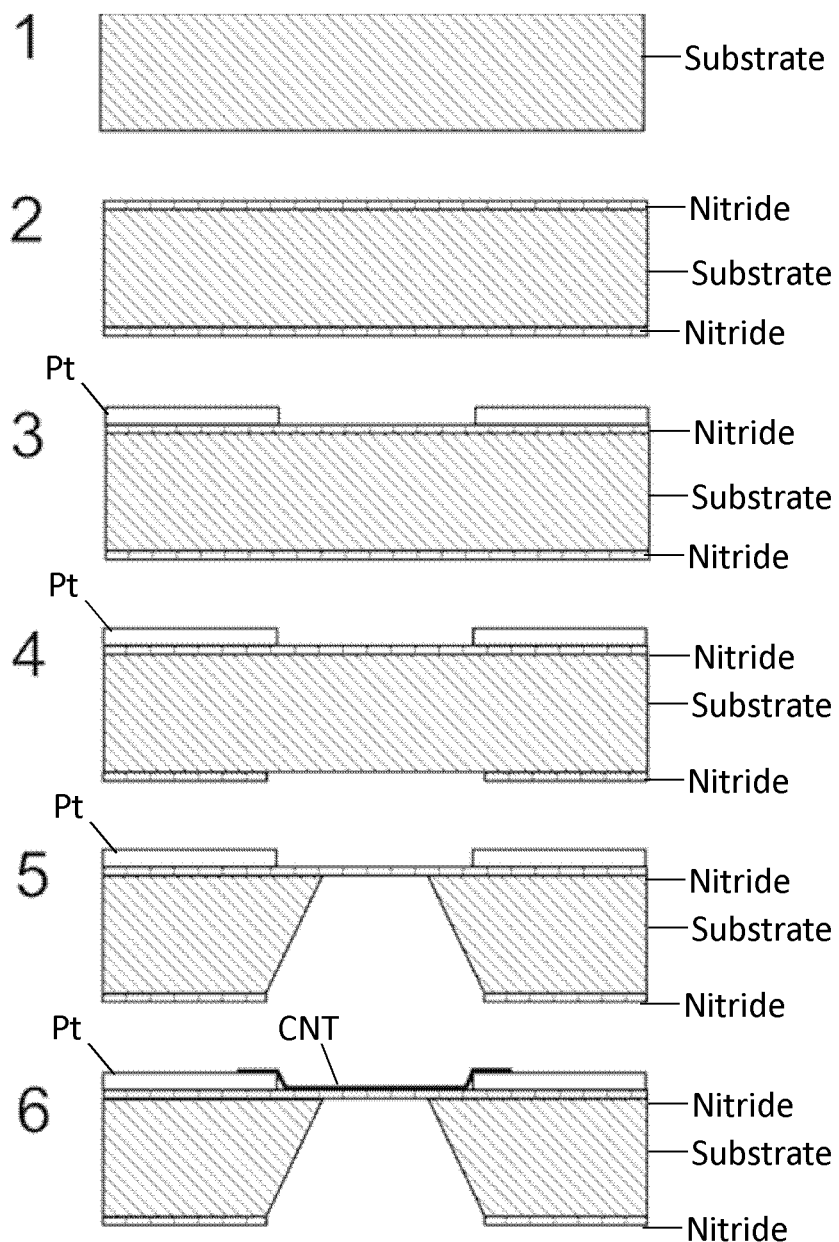
FIG. 2. Example of nanotube-aligned nanopore device fabrication. (1) The devices are made on a double-side-polished high resistance silicon (>10 kΩ-cm) substrate to minimize capacitive coupling between substrate and device. (2) 16 nm of high-quality thermal nitride is grown on both sides of the substrate. (3) 25 nm-thick platinum electrode pairs, separated by 20 μm are deposited following the deposition of a 5 nm chrome adhesion layer. This layer also contains the alignment marks for all remaining layers. (4) Using backside alignment, a window is patterned on the back of the wafer in the device region, and the nitride there removed by reactive ion etching (RIE) ($CHF_3/O_2$). (5) The device is placed in 20% potassium hydroxide (KOH), to etch open a window from the bottom of the device by etching the silicon substrate. (6) Nanotubes are grown from a catalyst on the surface, are grown from one electrode to a nearby electrode, and/or are transferred from a growth substrate to the device substrate, using standard techniques (e.g., grown on Y-cut quartz, coated in PMMA, lifted off in KOH, mechanically transferred, PMMA removed). (7) Microfluidic channels are placed on top and bottom. The channels are made from polydimethylsiloxane (PDMS) clamped between acrylic holders with larger fluidic channels that were formed using a $CO_2$ laser and hotpress bonding. This apparatus can then attach to standard microfluidic tubing. (8) A nanopore is etched by flowing 100:1 (49%) HF below the device, while applying a positive voltage to the nanotube, relative to the HF solution. Feedback may be used to tell when the etch has completed. An electrode in a solution is placed in the top microfluidic channel. An additional dielectric layer such as alumina may be required on top of the nanotube, to avoid charge screening by the nanotube. The voltage on this top electrode may be swept periodically to determine whether a nanopore has formed. When a current is detected, the voltage on the nanotube is turned off, and the HF is flushed out with water. Various electrodes may be used in the solution, but we have found that copper in the lower solution, and gold in the upper works well. Alternatively, a self-limiting process may be used where the top solution is at a positive pressure relative to the bottom, and when a pore forms, the pressure forces a chemically inert liquid (e.g., deionized water) from the top channel to the bottom, stopping the etchant from further etching the pore.
Figure 2:
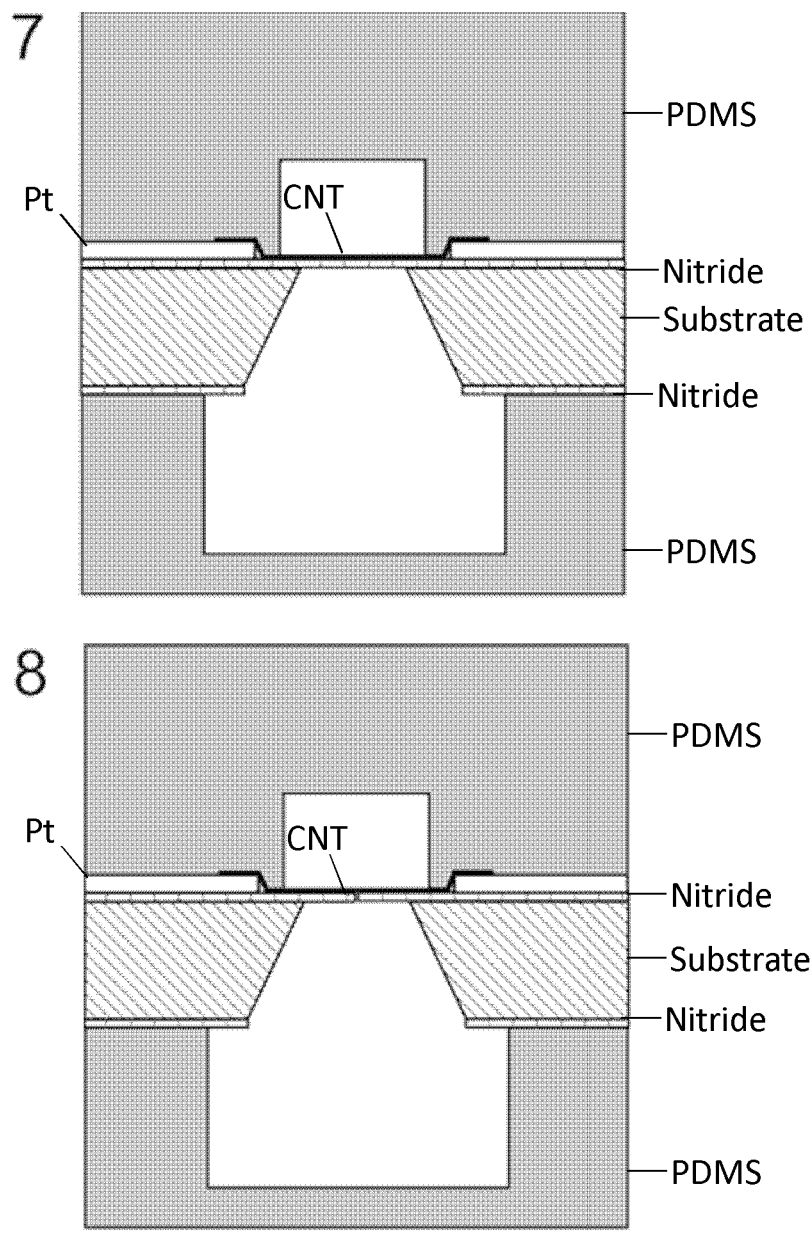
Figure 21:
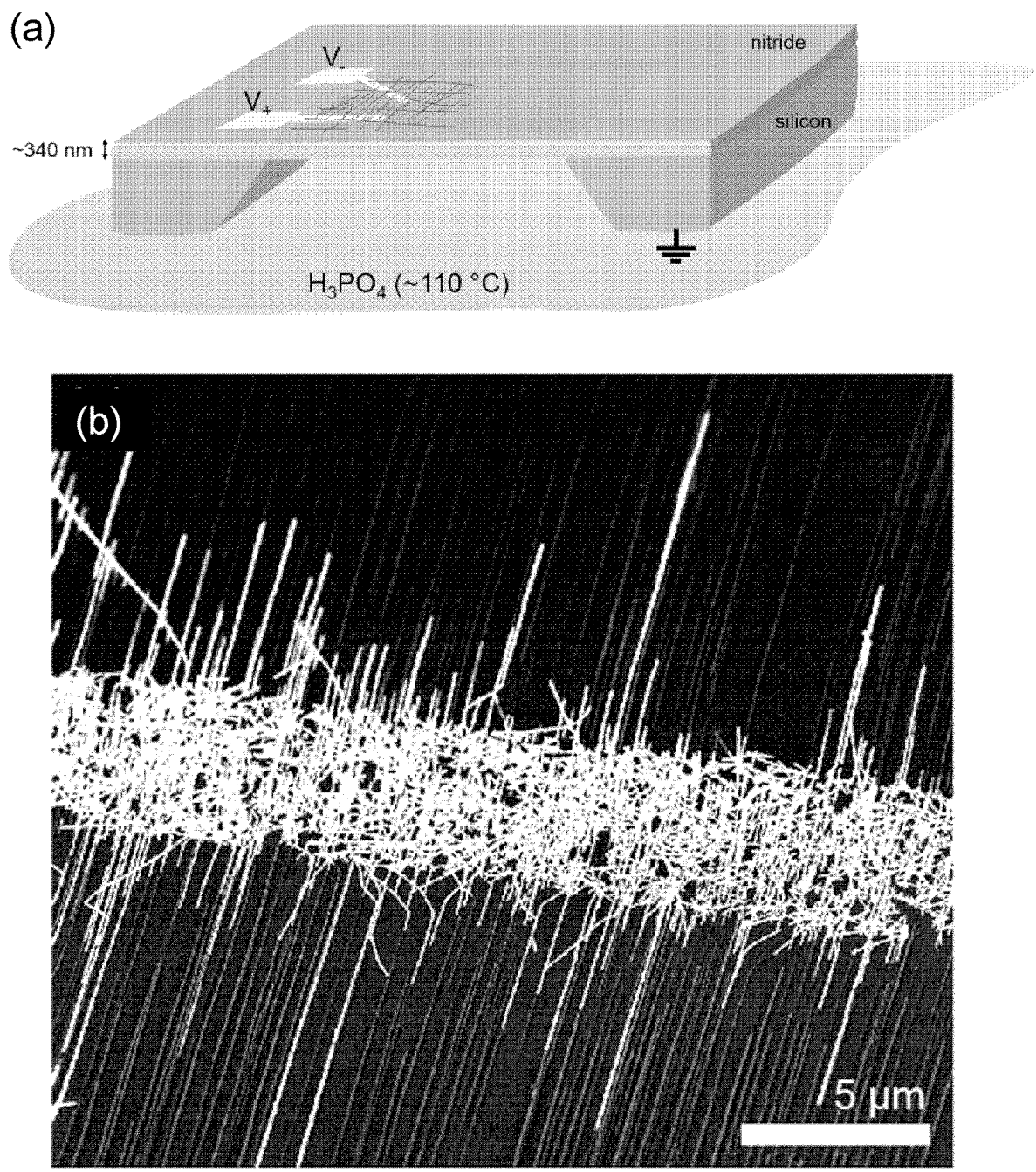
FIG. 21. Proof-of-principle study of voltage-assisted etching. (a) Schematic of silicon nitride membrane with electrodes and a nanotube network above the membrane, and hot phosphoric acid below. Voltages are applied to the two electrodes, relative to a grounded solution. (b) SEM image of aligned carbon nanotubes growing from a patterned catalyst line on Y-cut quartz, before being transferred to the nitride membrane. Catalyst lines are patterned in rows, 50 µm apart, and nanotubes are long enough that the nanotubes form a continuous network.

To explore the nanotube-localized etch process, the device in FIG. 21 (a) is made, using process steps similar to those shown in FIG. 1. A 340 nm silicon nitride membrane is thermally grown on a double-side polished silicon wafer. The back of the wafer is patterned with squares, and the nitride in those locations is removed using reactive ion etching. 25% KOH at 85° C. is used to remove silicon in the square window region, and a shadow mask (stencil) is used to sputter-deposit gold electrodes onto the top surface. Finally, a conducting network of nanotubes, shown in FIG. 21 (b), is transferred from a quartz substrate to the membrane, using a similar procedure to that in FIG. 1.

The device is placed in a shallow bath of phosphoric acid on a heating chuck set to 110° C., and the electrodes are electrically connected to voltage sources using electrical probes. 25 V is applied to one electrode and −25 V to the other, while grounding the phosphoric acid solution.

Figure 22:
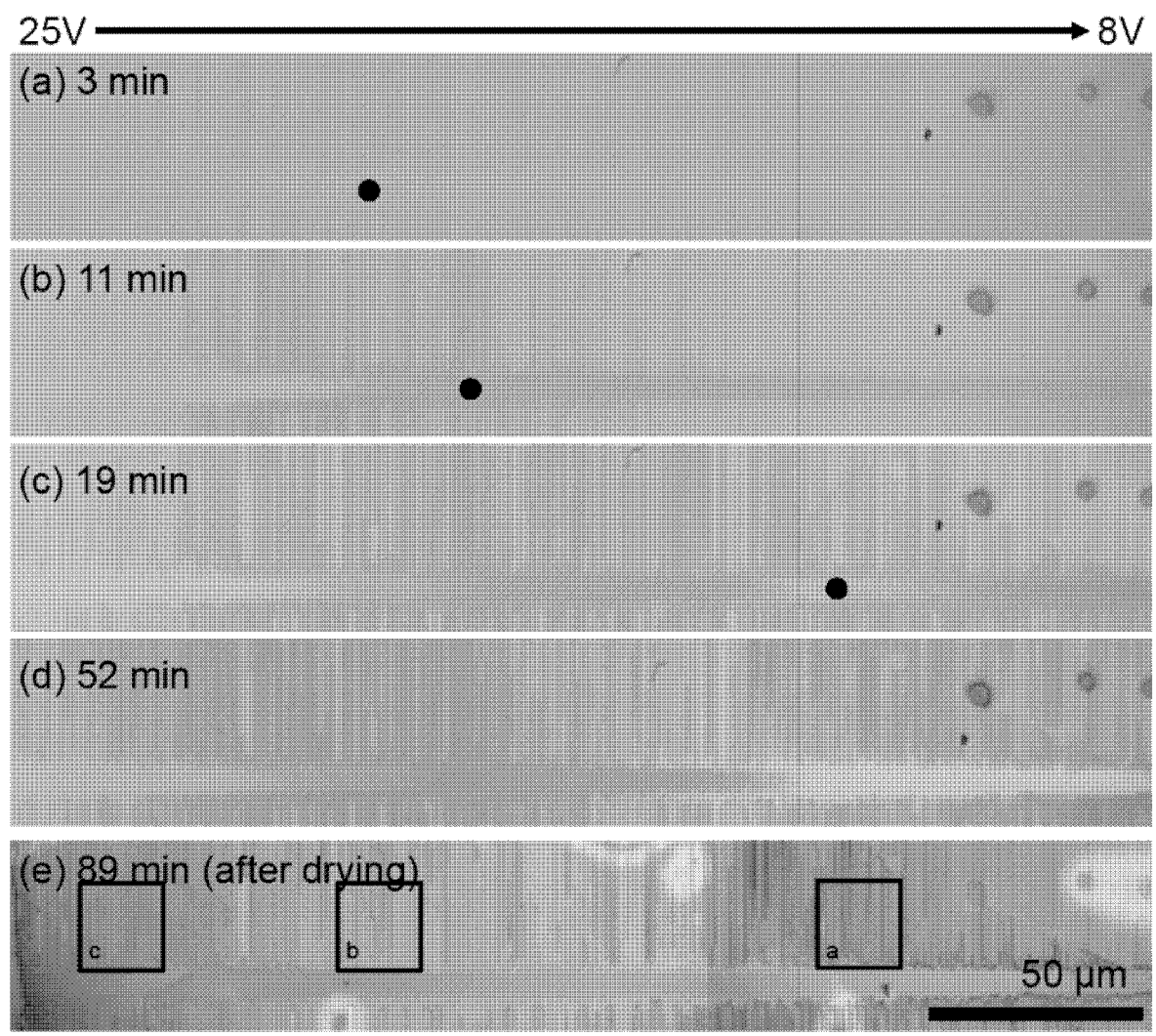
FIG. 22. Time series of voltage-assisted etch. (a-d) Optical images of nitride membrane during phosphoric acid etch at 110° C. Due to thin-film interference, the etch depth can be monitored optically. Thin vertical lines are etched regions under nanotubes; the wide horizontal line is etching under the catalyst line. The voltage being applied to the nanotubes decreases from left to right, from approximately 25 V to approximately 8 V. The etch rate is both voltage and time dependent, with the deepest etch location moving toward the right over time (black dots). The etch rate in the deepest location is 3 nm/minute, more than 3 times faster than the etch rate far from the nanotubes. (e) After the etch is complete (i.e. breaks through the membrane in a few locations), it is dried and imaged using AFM from the bottom in locations a-c (see FIG. 23).

FIG. 22 shows a time series of optical microscope images of the nitride membrane during the etch, near the positive electrode. A catalyst line spans the image horizontally, and nanotubes span it vertically. At the left of each image, the voltage is 25 V, and is expected to decrease approximately linearly to about 8 V at the right. Due to thin-film interference, as the thickness of the membrane changes, the color also changes, and from the color, the thickness can be estimated. The time series shows clearly that the etch is indeed enhanced by the applied voltage, with the regions under the nanotubes and catalyst lines becoming thinner, and changing color much more quickly than the regions between nanotubes. The etch rate also varies with voltage, with the maximum observed etch rate in (a-c) occurring between 25 V and 8 V, suggesting the existence of an optimal voltage for etching, at least for the given device and experimental conditions. These voltages correspond to electric fields in the membrane of approximately 20-70 mV/nm. At the deepest etch location, the etch rate was approximately 3 nm/minute, which is more than 3 times the etch rate in the regions far from the nanotubes. The etch was not enhanced at all near the negative electrode. The phosphoric acid broke through the membrane after about an hour, and the etch was stopped after 89 minutes, and the membrane rinsed and dried.

Figure 23:
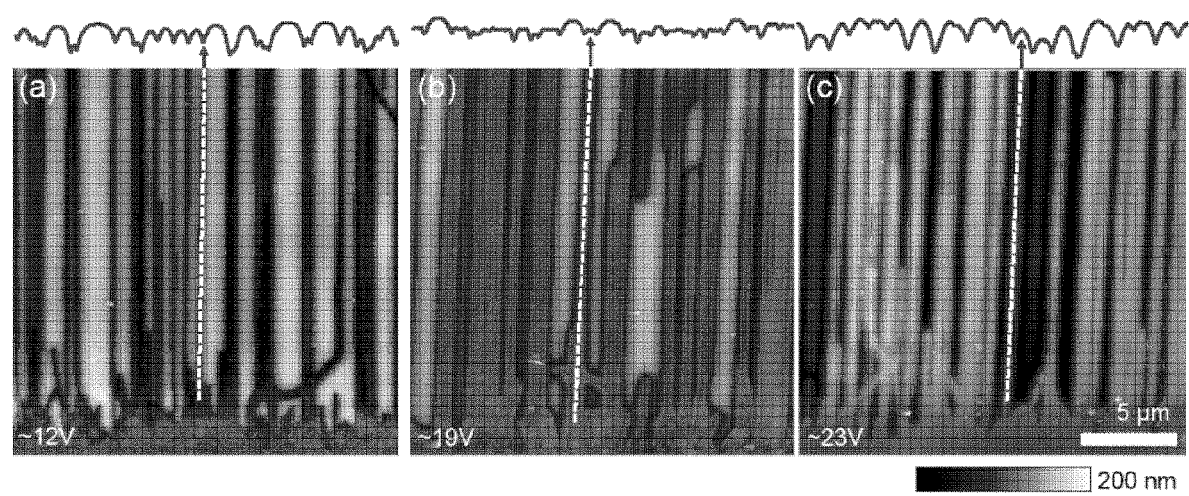
FIG. 23. Voltage-dependent etch profiles. (a-c) AFM height images of the etched underside of the nitride membrane from FIG. 22. Dashed lines indicate a nanotube location. Horizontal line cuts across the top of each image are shown above each image. (a) At low voltages, the etch is enhanced directly under the nanotube. (b) At mid-range voltages, the etch is relatively flat near nanotubes. (c) At high voltages, the regions adjacent to the nanotube etch faster than the region under the nanotube.

In order to characterize the localization of the etching of the membrane in the proximity of the nanotubes, the membrane was flipped upside-down, and the bottom was imaged by atomic force microscope (AFM). Three of the imaged locations are indicated by boxes in FIG. 22 (e), and the AFM images are shown in 2.3. FIG. 23 is mirrored relative to FIG. 22, since it was recorded from the bottom of the membrane while FIG. 22 was taken from the top. FIG. 23 shows the height profile of the etched membrane on the underside across from the nanotube locations. Examples of nanotube locations are indicated by dashed lines in each image. Line cuts taken from the top of each image are shown above each image, indicating that at lower voltages (a) the nanotube locations are etched more quickly than the regions between nanotubes, while at higher voltages (c) the nanotubes are etched more slowly relative to the surrounding nitride. Between these two extremes (b), the etch profile is relatively flat with nanotube locations being etched more slightly more quickly than the surrounding regions. This voltage-dependent pattern is indicative of an etching process that is dependent upon the surface charge distribution induced by the nanotube voltage, with a preferred charge range, above which or below which the etch rate is substantially reduced.

Figure 24:
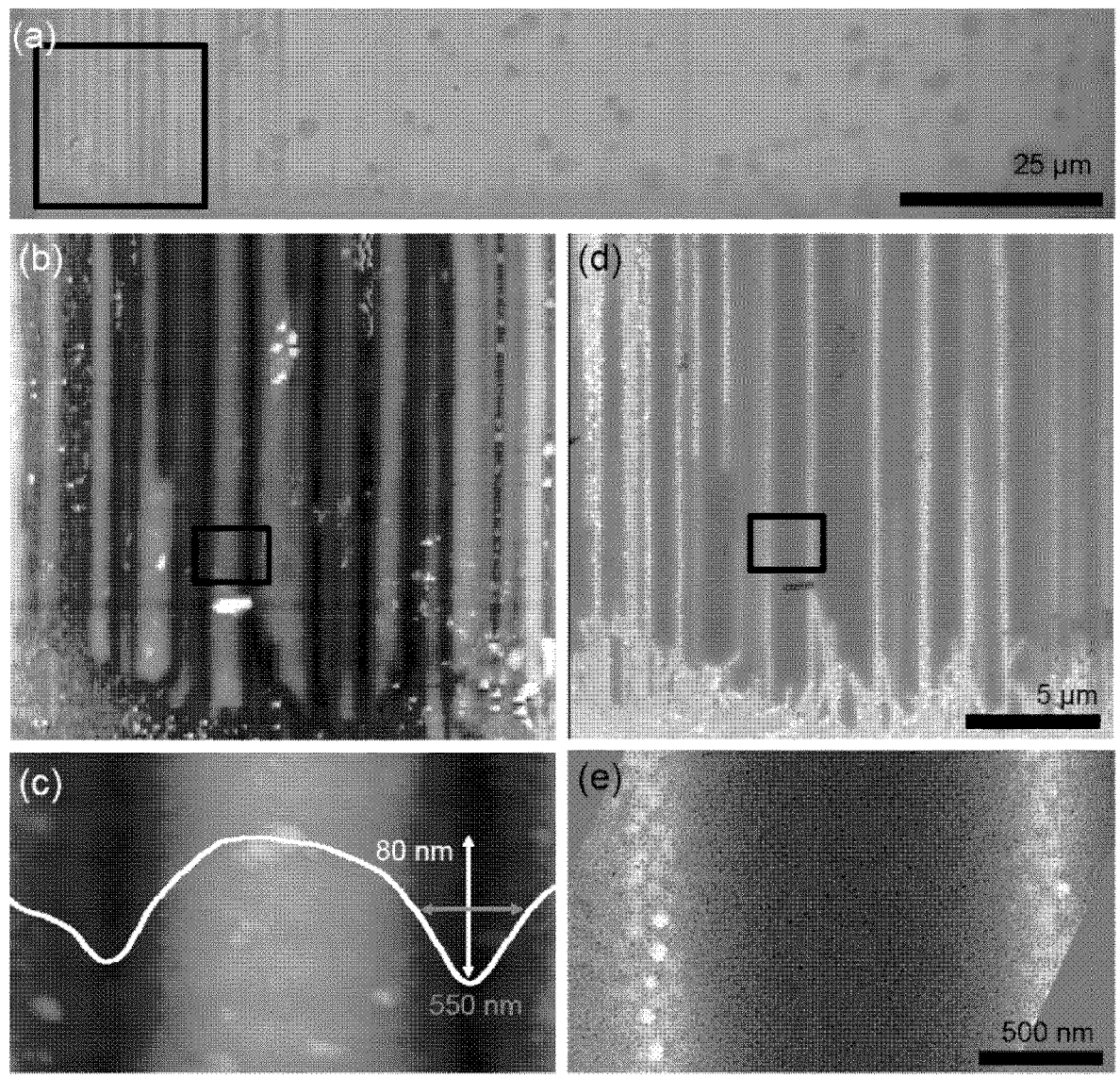
FIG. 24. Characterizing voltage-assisted etched membranes. (a) Optical image of a silicon nitride membrane after an approximately 43 minute etch in hot phosphoric acid at an alternating voltage of 20 $V_{AC}$. The location imaged at higher resolution is marked with a square. (b) AFM image showing that the etch is enhanced near the nanotube locations. (c) TEM image of the same region as in (b). (d) 80 nm-deep trenches, centered at nanotube locations. Overlaid in white is a line average across the whole image (e) TEM reveals that etched trenches consist of a series of etched pits.

FIG. 24 shows a region of a phosphoric acid-etched membrane that was (a) imaged optically, (b-c) by AFM, and (d-e) by transmission electron microscopy (TEM). AFM reveals that these trenches centered at nanotube locations are approximately 80 nm deep, with full-width at half-maximum of 550 nm. TEM indicates that the localized etch occurs somewhat non-uniformly, with the trenches consisting of a series of etched pits of various depths, having diameters of approximately 50 nm (bright, circular spots in (e)). It is expected that this is the result of a surface-roughening effect, where, due to the surface potential's non-linear dependence on membrane thickness, as a region becomes thin, the surface potential becomes larger and the etch rate accelerates. This likely also contributes to the ability to form a single nanopore rather than an etched slot.

With a thinner membrane, and a more refined etch procedure similar to that in Example 1, single <4 nm nanopores, localized to a single nanotube can be achieved with the hot phosphoric acid system.

Figure 25:
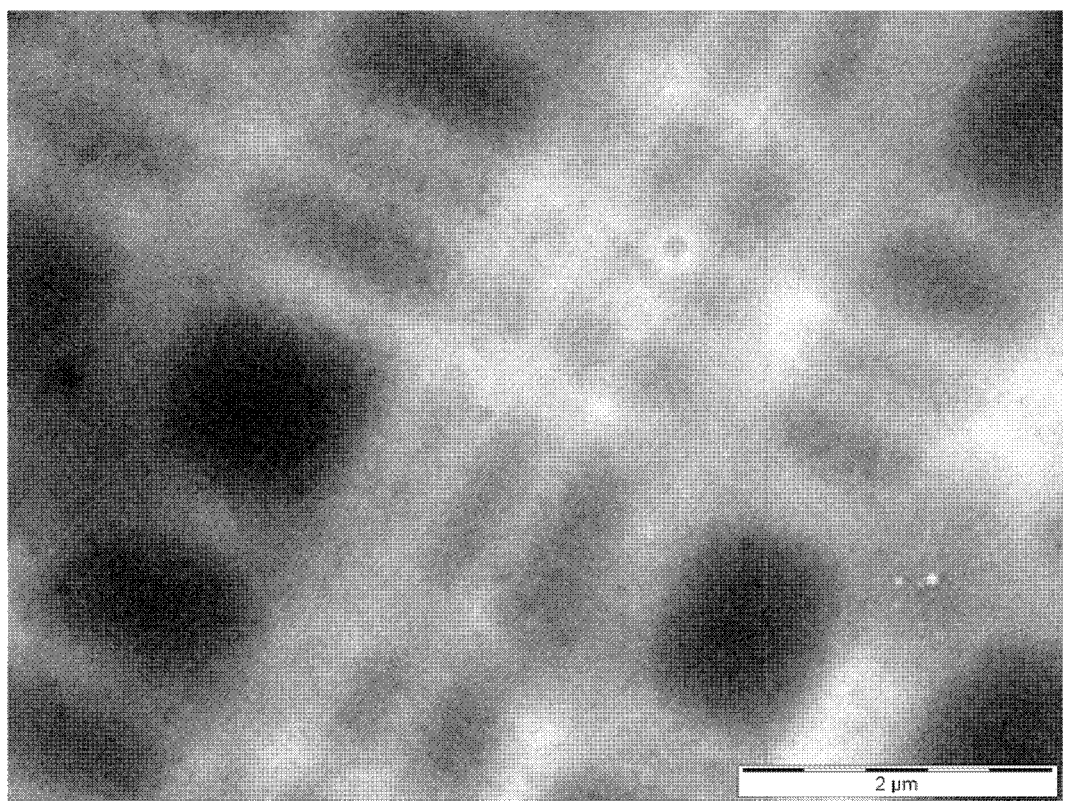
FIG. 25. TEM image showing a nitride membrane that has been locally-thinned in regions near a mesh of perpendicular carbon nanotubes (not visible). Where the nanotubes intersect, the image appears brighter, indicating that the etch of the membrane at these intersection points has been enhanced.

The etch rate can also be enhanced at the intersection between two nanotubes. FIG. 25 shows a TEM image of a membrane on which a mesh of perpendicular nanotubes was placed, and a voltage-assisted phosphoric acid etch was performed at 110° C. with 5V applied to the nanotubes relative to a grounded solution. After 173 minutes, a nanopore formed in the membrane (not shown). The etch was found to be enhanced underneath the membrane nearest the nanotubes, at a relatively low electric field across the membrane of approximately 10 mV/nm.

In FIG. 25, many of the regions where the nanotubes intersect are brighter than surrounding regions indicating that the etch rate is largest in these locations. This suggests that this etch method may be used to localize a nanopore to the intersection between nanoelectrodes, which is a geometry that may be used in, for example, an electron-tunneling-based nanosensor.

When our phosphoric acid-based etch-localization procedure is repeated at lower temperatures, e.g. <60° C., the etch rate is greatly reduced and localized etching is not measureable after hours, indicating that the chemical activity of the etchant can play an important role in the localized etching process.

Example 3

FIG. 7 shows a schematic device cross-section of a device used for localizing a nanopore to a nanotube, along with the circuit elements used for biasing the nanotube and employing ionic feedback. With minor modifications, this device configuration can be used for many of the different etch and detection methods disclosed herein.

A nanotube on top of a 16 nm-thick silicon nitride membrane is connected in series with a 10 GΩ resistor to ensure that the entire nanotube is at the applied potential, $V_{nt}$, relative to a grounded HF solution beneath the membrane. A separate voltage, $V_{tg}$, can be applied to a gold top gate, and the ionic current generated (if a nanopore has formed) is monitored by a current preamplifier connected to a copper wire in the HF solution.

To achieve sharp localization (i.e. a small nanopore), the etch may be completed while applying a very small voltage (e.g. <1 V), but for a thick membrane this may not lead to etch enhancement, so the entire membrane will become thinner, risking nanopore-formation away from the nanotube. To achieve (moderate) localization while the membrane is thick, a large voltage (e.g., 10 V) may be applied. For these reasons, the etch may be performed in two stages. In the first stage, the voltage on the nanotube is swept to 6-10 V and back down again in 0.2 seconds, as shown in FIG. 8 (b). This stage is brief, and intended to thin the membrane, but not create a nanopore. In the second stage, the voltage is left at 0.2-0.5 V for 5 minutes. It is during this stage, when a low voltage is on the nanotube, that nanopore formation is most desirable. The low voltage on the nanotube is intended to give narrow localization, and to minimize the risk of HF damaging the nanotube when the nanopore forms. During this second stage, the top gate voltage is swept to −1.4 V (at which, based on measurements, the copper-gold electrode pair may be electrochemically active), then back to zero in 0.2-0.4 second once every 15 seconds, to monitor for nanopore formation. This process (stages 1 and 2) is then repeated for approximately 20-60 minutes until a nanopore forms.

FIG. 8 (c) shows three consecutive −1.4 V top gate sweeps in stage 2 of the etch, after 52 minutes has elapsed. The first of these is very typical: an approximately 20 pA step occurs as the voltage ramp switches from sweeping downwards to sweeping upwards. The second panel shows the same sweep 15 seconds later. Here, ionic current (through a nanopore) is distinguishable above the noise, when the gate voltage is at −1.4 V. By the time another 15 seconds has gone by, the ionic current is dramatic, having decreased to −200 pA at −1.4 V.

Once a nanopore has formed, the dielectric layer may be etched before the HF can reach the top gate and thus before an ionic current can be detected. This typically takes 1-2 minutes, for a 25 nm-thick dielectric consisting of silicon dioxide and/or aluminum oxide, and an HF solution at 100:1-400:1 (here, 400:1). Thus, while the nanopore formation is detected at 52.25 minutes, the nanopore likely etched through during or slightly after the nanotube sweep at 50.5 minutes. Once the nanopore formation is detected, the voltages are set to zero, the circuit is disconnected, and the HF solution is flushed out with a chemically-inert liquid, such as deionized water, thus stopping the etch.

FIG. 8 (d) shows the resulting nanopore as imaged by TEM. Three different levels of magnification indicate that only a single nanopore has formed, and the highest magnification shows that the nanopore is 10 nm in diameter, and aligned to a nanotube. The dielectric within approximately 300 nm of the nanopore has been etched by the HF (after nanopore formation), and is observed as a brighter region in the first two panels of FIG. 8 (d). This usually enables a determination whether a nanopore has formed at its expected location (e.g., aligned to the nanotube) at low magnification, or even optically, as indicted by the arrows, and inset. This may be important because even at 40 keV, the electron beam in the TEM almost always renders the nanotubes nonconducting, unless imaged at very low magnification (where the nanotube is not visible). Note also, that while TEM imaging of this sample precludes the possibility that it now conducts, it did survive the entire etch process, as can be observed by the constant 20 pA current registered at the nanotube preamp throughout the measurements in FIG. 8 (c).

To optimize etch localization, without destroying the nanotube, another feature that was used in this example is to do a few higher-voltage ramps prior to starting the repeated two-stage process described in this example. Typically, during the first two cycles of the two-stage process, the nanotube voltage is swept to-and-from 10 V over 0.2-0.5 second, then for the remaining nanotube sweeps, the voltage is reduced to 6-7 V. This likely thins the membrane locally, making it far more likely that the nanopore will form near the nanotube. If a third sweep to 10 V is done, roughly 50% of the time a nanopore will form during that sweep, destroying the nanotube. This suggests that the membrane has been thinned significantly by the first two sweeps.

The etching process outlined in this example is very consistent for a given round of device fabrication, and the correct HF concentration. The etch parameters may be adjusted if a different membrane thickness is used, and/or if the thickness of the dielectric layer between the nanotube and top gate electrode is changed. Once these parameters have been optimized for a given fabrication round, a yield of approximately 50% is common for achieving a single <15 nm nanopore aligned to a nanotube that remains electrically conducting.

Example 4

FIG. 9 shows an example of a similar etch procedure to that shown in FIG. 8, and similar circuit to that shown in FIG. 7, but using lower voltages applied to the nanotube. In this example, the "window" regions (lighter circles in FIG. 9 (b)) were thinned from 34 nm to approximately 20 nm using reactive ion etching. This likely roughened the surface, leading to regions that are thinner than 20 nm. The etch is performed by ramping the nanotube voltage from 0.5 V to 4 V and back in 1.5 seconds, where it is left at a resting voltage of 0.5V for 2 minutes. While the nanotube is at its resting voltage, a gold top gate is periodically swept to-and-from 1.5 V until an increase in current at a copper electrode in the HF solution is registered, as shown in FIG. 9 (a). At this point, a nanopore has formed, no further voltages are applied, and the HF is flushed out using a chemically-inert liquid, such as deionized water.

Example 5

The nanotube itself can be used to detect the formation of a nanopore. This may have advantages over using a separate top gate to detect the formation of the nanopore. Firstly, the formation of the nanopore can be detected more rapidly (before the dielectric above the nanotube has been etched away). Secondly, when using nanotube-based detection, the dielectric above the nanotube does not have to be susceptible to etching by the same etchant that etches the membrane and thus the etch process can more easily be separated into two steps. For example, HF can be used to etch a nanopore in a silicon nitride membrane, then KOH can be used to etch through an alumina dielectric layer above the membrane and nanopore.

Figure 10:
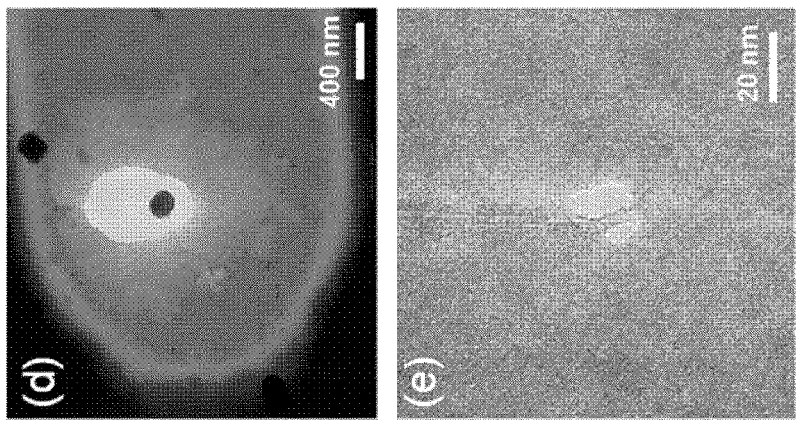
FIG. 10. Nanotube-based detection of nanopore formation. (a) To create a nanopore a positive voltage is periodically applied to the nanotube, while current in the nanotube is (optionally) monitored through a 1 GΩ resistor. (b) The formation of the nanopore is detected by an increase in the magnitude of the current upon applying a negative voltage to the nanotube, in this instance after 19 minutes and 16 seconds. (c) The alumina dielectric above the nanotube is removed by flowing 0.25 M KOH below the membrane while periodically sweeping a voltage applied to a KCl solution above the membrane. Once the KOH has etched away the dielectric above the nanopore, an increase in the magnitude of ionic current is detected. (d) A TEM image reveals that the alumina has been etched by the KOH in the region surrounding the nanopore (bright region). (e) at the center of the bright region in (d) is an approximately 20 nm nanopore spanned by a carbon nanotube.
Figure 10:
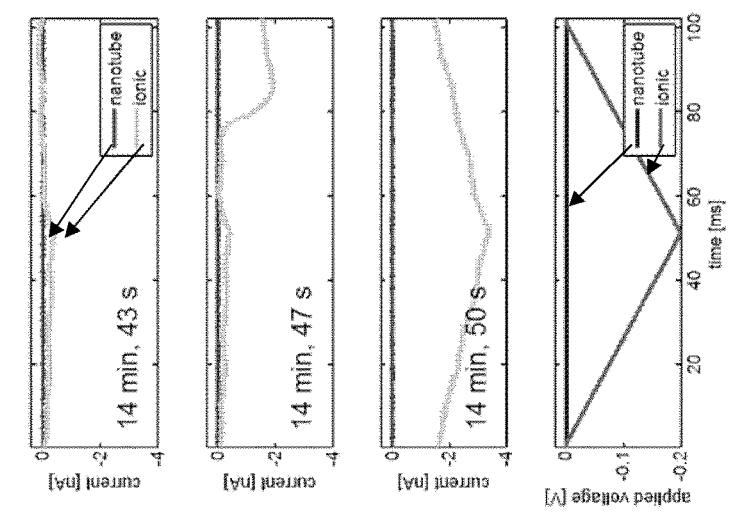
Figure 10:
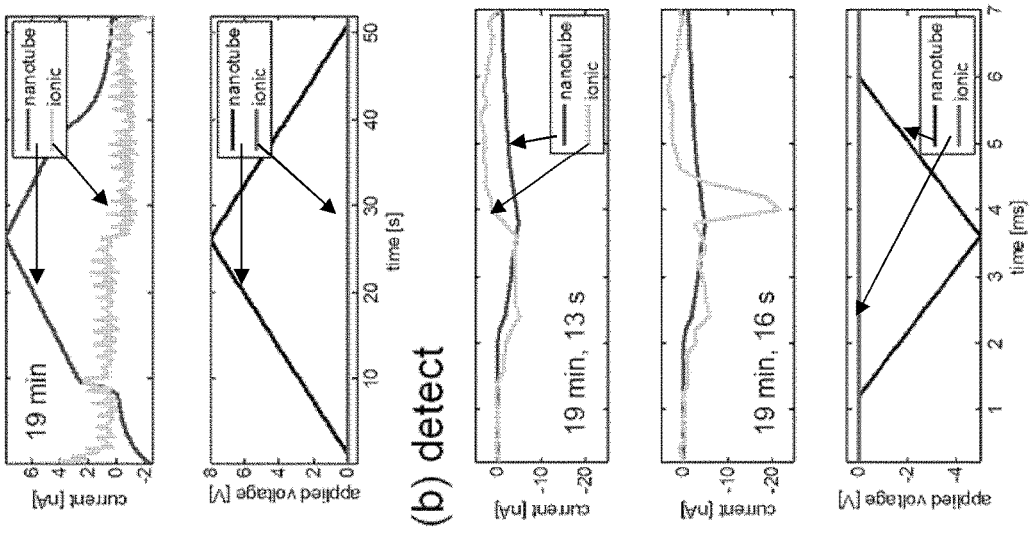

FIG. 10 shows an example of an etch process in which the nanotube is part of the nanopore detection circuit. As in previous examples, a positive voltage is periodically applied to the nanotube, an example trace from which is shown in FIG. 10 (a). In this instance, the circuit is the same as in FIG. 7, except with the gold top gate being replaced by an approximately 1 mM KCl solution having a voltage applied to it via a silver-chloride electrode (0 V for most of the process). Every minute the nanotube voltage is swept to positive 8V. After 19 minutes and 16 second a nanopore forms.

The formation of the nanopore (or a pit or other feature in the membrane) is detected via a negative voltage periodically applied to the nanotube, relative to the 400:1 HF solution underneath the nitride membrane, connected to a transimpedance amplifier. FIG. 10 (b) shows the applied voltages as well as the measured currents during the final two traces of the process. At 19 minutes, 13 seconds, the nanopore has not yet formed. 3 seconds later, upon applying −5 V to the nanotube, a negative current is measured at the preamplifier (flowing from the nanotube into the solution, via a newly-formed hole in the nitride layer). After detection, no further voltages are applied and the HF is flushed out using a chemically-inert liquid, such as deionized water.

To remove the alumina dielectric layer remaining over the nanotube from the region near the nanotube, to fluidly connect the top and bottom microfluidic channels via the nanopore, 0.25 M KOH is flowed underneath the membrane. Every approximately 3 seconds, the voltage on an electrode in the top KCl solution is swept to-and-from −200 mV, and the current at the copper electrode below the membrane is monitored. FIG. 10 (c) shows the last 3 of these traces. After 14 minutes 47 seconds, the dielectric is sufficiently removed that ionic current flows from beneath the membrane to above the membrane, via a nanopore.

FIGS. 10 (d) and (e) show TEM images of the resulting device and nanopore at two levels of magnification. In FIG.

10 (*d*) it can be seen that the alumina has been removed from near the nanotube in an elliptical 500 nm by 800 nm region. At the center of this region is a nanopore, spanned by a nanotube, as shown in FIG. 10 (*e*).

Example 6

Another method of determining whether a nanopore has formed that may not rely on ionic current or large voltages applied to either the nanotube or the solution involves using the nanotube as a field-effect transistor (FET). Carbon nanotubes (and other field-effect sensors) have electrical conductance that depends on their electrostatic environment. If that environment changes (e.g., by the formation of an adjacent nanopore) the conductance can change, yielding a means of electrically detecting and measuring that change.

Figure 11:
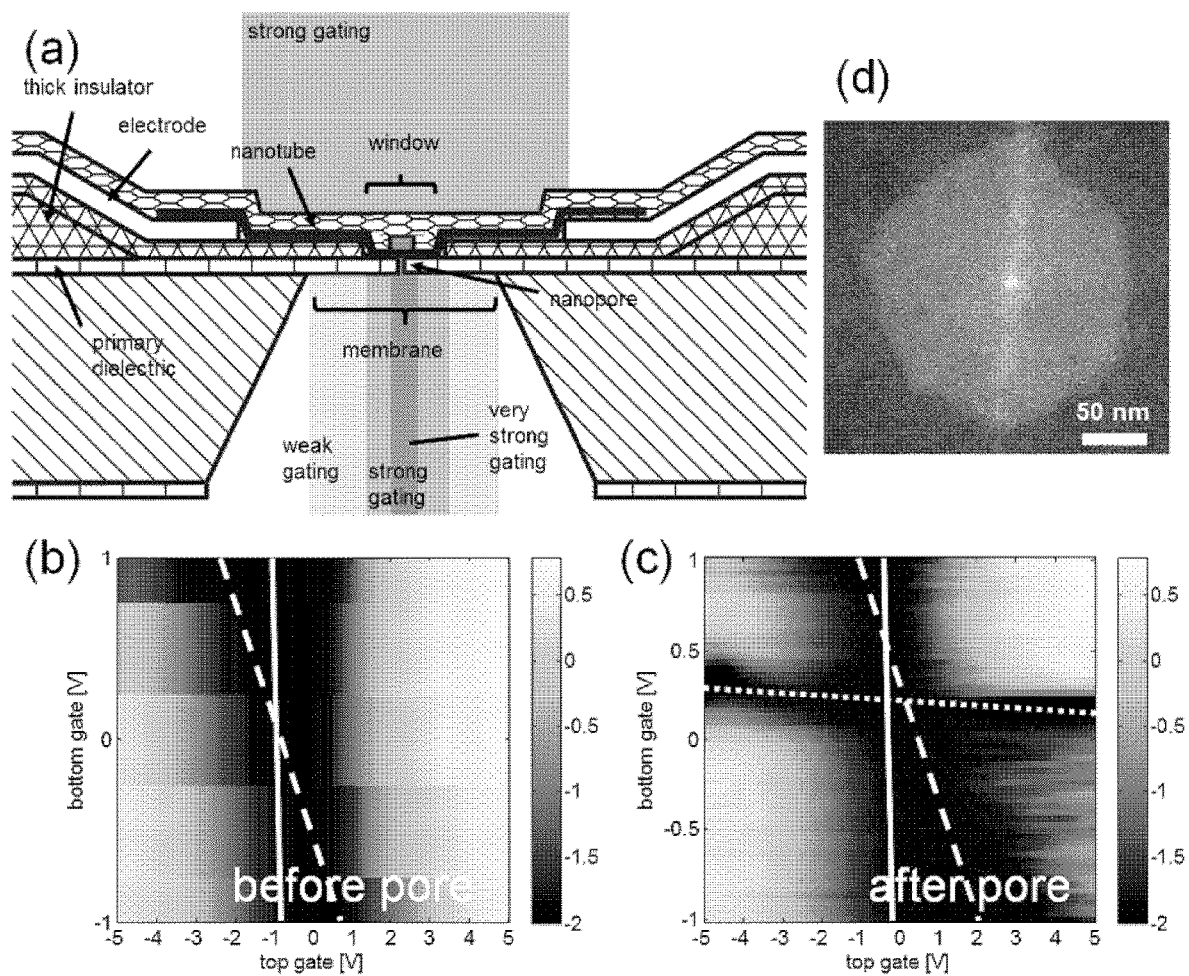
FIG. 11. Detecting nanopore formation by local gating of a nanotube FET. (a) Schematic of the device and strength of FET gating. (b) Ionic current (in $\log_{10}$ (nA)) of a semiconducting nanotube at 10 mV bias as a function of voltage applied to top and bottom gates (the bottom gate, here, is an ionic solution) before nanopore formation. (c) After nanopore formation the nanotube is in contact with the bottom solution, which strongly electrostatically gates the nanotube FET (approximately 100 mV/decade). (d) TEM image of the resulting nanopore, and surrounding "pocket" (lighter shade) etched into the alumina dielectric above the nitride membrane.

FIG. 11 (*a*) shows a schematic of a nanotube device, after a nanopore has been formed in a primary dielectric layer (e.g. silicon nitride). Immediately after nanopore formation, there can be many different regions of the nanotube that will have different "gating" responses to voltages applied above and below the membrane, as indicated by the shaded pink and blue regions. The thinner the dielectric, and the larger the dielectric constant of the material between the nanotube and the top or bottom gate electrode (or solution), the more strongly the nanotube will be "gated" (e.g., have an electrical conductance that changes in response to an applied voltage).

The gating characteristics of the nanotube before nanopore formation is shown in FIG. 11 (*b*). The nanotube device is semiconducting, so it can be gated to show n-type or p-type conductance, with a non-conducting bandgap region at gate voltages between these regions. In this example, there are features that are indicative of two regions of the nanotube having different gating characteristics. One of these only responds to changes in the top gate, or the region of the nanotube near the electrodes which is only gated by the top solution. The center of the bandgap for this region is indicated by the vertical solid line in FIG. 11 (*b*). The other region responds to both the top and bottom gate, but responds to the bottom gate more strongly than the top gate. This is the region is the "membrane" region which is exposed to both the top and bottom solution, and indicated by the dashed line.

After nanopore formation, the gating characteristics change significantly. In addition to the original two regions having distinct gating characteristics, once a nanopore has formed, the bottom solution is in direct contact with the nanotube, and thus strongly gates the nanotube. FIG. 11 (*c*) shows the current through the nanotube as a function of the top and bottom gates. The primary features seen in FIG. 11 (*b*) are still observed, but a third feature that is strongly gated by the bottom gate appears. This is the small region near the nanopore where the bottom solution is now in contact with the nanotube (and is coupling electrostatically, without significant leakage current). The center of the bandgap for this region is indicated by the dotted line. The appearance of this feature makes it clear that a nanopore has formed, so the etch may be stopped, and etchant flushed out.

For this particular example, the 400:1 HF that was used to etch the nanopore was periodically flushed out and replaced with 1 mM KCl and the copper electrode was exchanged with a silver-chloride electrode to test the gating characteristics for an indication of the presence of a nanopore. This may not be necessary though, as similar gating can be done using the HF (with some additional risk of causing a nanopore to form when performing the gating measurements).

FIG. 11 (*d*) shows the resulting nanopore, and etched "pocket" region of the alumina dielectric. In this example, the etch was stopped before the alumina was fully removed, leaving a "nanochamber" connected via the nanotube-aligned nanopore to the bottom solution, while electrically isolated from the top gate or a top solution. The etch could be completed with a weak acid or base (e.g. 0.25 M KOH), or this pocket geometry could be used for molecule or ion detection measurements.

Example 7

FIG. 12 shows an SEM image of a simpler device geometry for nanotube-aligned nanopore formation. In this example, electrodes are patterned onto a silicon nitride membrane. Aligned arrays of nanotubes are transferred to the device substrate using methods described elsewhere in this document (e.g., FIG. 1). A suspended silicon nitride membrane is opened up via a KOH etch through a back-side patterned silicon nitride mask, using methods described elsewhere in this disclosure. A nanopore can be formed in the silicon nitride membrane using methods described elsewhere in this disclosure. An example of such a nanopore aligned to a nanotube is shown in FIG. 12 (*b*). Feedback to detect nanopore formation may be electronic, as previously described, or optical (e.g., by viewing under a microscope the leakage of solution through the nanopore), and then stopping the etch. Alternatively the etch may be performed without feedback, stopping the etch after a selected amount of time.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A method comprising:
   disposing at least one nanoscale electronic element capable of conducting electricity on or in a membrane disposed on a substrate, wherein the membrane is fabricated of a dielectric, semiconductor, or semimetal;
   contacting the membrane with an etchant; and
   applying a voltage to the nanoscale electronic element relative to another electrode in contact with the etchant such that at least one nanopore is etched through the membrane within 50 nm of the nanoscale element.

2. The method of claim 1, wherein a sign and/or a magnitude of the voltage is selected to locally affect etch rate of the etchant proximate the nanoscale electronic element.

3. The method claim 1, further comprising:
   applying a pressure to fluid on one side of the membrane relative to an opposite side of the membrane; and
   flowing the fluid through the nanopore after the nanopore is etched through the membrane, wherein the fluid does not substantially etch the membrane and decreases or halts etching of the membrane.

4. The method of claim 1, wherein the voltage is pulsed, ramped, constant, or a combination thereof.

5. The method of claim 1, further comprising detecting formation of the nanopore by applying a voltage to a detection electrode and monitoring current flowing to or from the detection electrode, wherein the detection electrode is separate from the nanoscale electronic element, and wherein the detection electrode is positioned outside the etchant and, optionally, applying a voltage to a solution on a side of the membrane opposite the etchant using the detection electrode.

6. The method of claim 1, further comprising stopping etching of the nanopore using feedback.

7. The method of claim 6, wherein the feedback is electrical and is based on at least one of:
changes in current from one side of the membrane to an opposite side of the membrane;
changes in current and/or conductance through the nanoscale electronic element; and/or
changes in current flowing between the nanoscale electronic element and the electrode in contact with the etchant.

8. The method of claim 6, wherein the stopping occurs when a magnitude of a current exceeds a threshold, when a rate of change of a current or derivative of current with respect to time exceeds a threshold, when a shape of a plot of current through the nanoscale electronic element as a function of voltage of a detection electrode and/or the electrode in contact with the etchant changes, or after a designated time.

9. The method of claim 1, further comprising stopping etching of the nanopore by replacing the etchant with a fluid that is less chemically-reactive than the etchant and/or changing the voltage to the nanoscale electronic element.

10. The method of claim 1, wherein a plurality of the nanopores is formed.

11. The method of claim 1, wherein during etching of the nanopore an average electric field along a shortest distance between any region of the nanoscale electronic element disposed on or in the membrane and the etchant is less than 0.1 V/nm.

12. The method of claim 1, wherein the applying the voltage comprises applying a first voltage whereby the membrane is thinned and applying a second voltage smaller than the first voltage to form the nanopore.

13. A nanopore-containing substrate, comprising:
a substrate;
a membrane disposed on the substrate having at least one nanopore, wherein the nanopore is configured to provide fluidic communication between opposite sides of the membrane;
at least one nanoscale electronic element disposed on or in the membrane;
wherein at least one nanopore in the membrane has been aligned to at least one nanoscale electronic element using the method of claim 1.

14. A nanopore-containing substrate comprising:
a substrate;
a membrane disposed on the substrate, wherein the membrane defines at least one nanopore through the membrane, wherein the nanopore is configured to provide fluidic communication between opposite sides of the membrane, and
at least one nanoscale electronic element that is disposed on or in the membrane, wherein the nanoscale electronic element is electrically conductive, and
at least one nanopore is self-aligned to at least one nanoscale electronic element, wherein the nanopore is formed by applying a voltage to the nanoscale electronic element.

15. The nanopore-containing substrate of claim 14, wherein the at least one nanopore comprises a plurality of nanopores and the at least one nanoscale electronic element comprises a plurality of nanoscale electronic elements.

16. The nanopore-containing substrate of claim 15, wherein the nanoscale electronic elements are self-aligned to 100% of the nanopores.

* * * * *